US011596632B2

(12) United States Patent
Yeleswaram et al.

(10) Patent No.: US 11,596,632 B2
(45) Date of Patent: Mar. 7, 2023

(54) JAK1 PATHWAY INHIBITORS FOR THE TREATMENT OF GASTROINTESTINAL DISEASE

(71) Applicant: Incyte Corporation, Wilmington, DE (US)

(72) Inventors: Krishnaswamy Yeleswaram, Landenberg, PA (US); Paul Smith, Wilmington, DE (US); Gregory F. Hollis, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/720,465

(22) Filed: Dec. 19, 2019

(65) Prior Publication Data
US 2020/0197399 A1 Jun. 25, 2020

Related U.S. Application Data

(60) Provisional application No. 62/901,377, filed on Sep. 17, 2019, provisional application No. 62/854,801, filed on May 30, 2019, provisional application No. 62/781,877, filed on Dec. 19, 2018.

(51) Int. Cl.
A61K 31/519 (2006.01)
A61P 1/00 (2006.01)
A61K 31/4155 (2006.01)
A61K 31/437 (2006.01)

(52) U.S. Cl.
CPC ........ A61K 31/519 (2013.01); A61K 31/4155 (2013.01); A61K 31/437 (2013.01); A61P 1/00 (2018.01)

(58) Field of Classification Search
CPC ........... A61K 31/519; A61P 1/00; A61P 43/00
USPC .................................................... 514/265.1
See application file for complete search history.

(56) References Cited

U.S. PATENT DOCUMENTS

| 8,765,734 | B2 * | 7/2014 | Huang ................. | A61K 9/0019 514/210.21 |
|---|---|---|---|---|
| 2010/0298334 | A1 | 11/2010 | Rodgers et al. | |
| 2011/0059951 | A1 | 3/2011 | Rodgers et al. | |
| 2011/0224190 | A1 | 9/2011 | Huang et al. | |
| 2012/0149681 | A1 | 6/2012 | Rodgers et al. | |
| 2012/0149682 | A1 | 6/2012 | Rodgers et al. | |
| 2013/0018034 | A1 | 1/2013 | Yao et al. | |
| 2013/0045963 | A1 | 2/2013 | Rodgers et al. | |
| 2013/0060026 | A1 | 3/2013 | Zhou et al. | |
| 2014/0005166 | A1 | 1/2014 | Rodgers et al. | |
| 2014/0121198 | A1 | 5/2014 | Li et al. | |
| 2014/0256941 | A1 | 9/2014 | Liu et al. | |
| 2014/0343030 | A1 | 11/2014 | Li et al. | |
| 2015/0065484 | A1 | 3/2015 | Yeleswaram et al. | |
| 2015/0344497 | A1 | 12/2015 | Zhou et al. | |
| 2017/0145044 | A1 | 5/2017 | Hudson et al. | |

FOREIGN PATENT DOCUMENTS

| WO | WO 2002/000196 | 1/2002 |
|---|---|---|
| WO | WO 2018/111327 | 6/2018 |

OTHER PUBLICATIONS

Sandborn, W.J. et al.: Safety and efficacy of ABT-494 (Updacitinib), an oral JAK1 inhibitor, as induction therapy in patients with Crohn's disease. Gastroenterology, vol. 152, pp. S 1308-1309, 2017.*
Sands, B.E. et al.: Peficitinib, an oral janus kinase inhibitor, in moderate-to-severe ulcerative colitis, results from a randomized, phase 2 study. J. Crohns Colitis, vol. 12, pp. 1158-1169, 2018.*
Andres et al., "Epidemiology and the natural course of inflammatory bowel disease," Gastroenterol Clin North Am., 1999, 28:255-281.
Argollo et al., "Novel therapeutic targets for inflammatory bowel disease," Journal of Autoimmunity, Jul. 12, 2017, 85:103-116.
Beattie et al., "Intestinally-restricted Janus Kinase inhibition: a potential approach to maximize the therapeutic index in inflammatory bowel disease therapy," Journal of Inflammation, 2017, 14:28.
Berge et al., "Pharmaceutical Salts," J Pharm Sci., 1977, 66(1), 1-19.
Bernado et al., "IL-6 promotes immune responses in human ulcerative colitis and induces a skin-homing phenotype in the dendritic cells and T cells they stimulate," Eur J Immunol., 2012, 42:1337-1353.
Bilal et al., "A systematic review and meta-analysis of the efficacy and safety of the interleukin (IL)-12/23 and IL-17 inhibitors ustekinumab, secukinumab, ixekizumab, brodalumab, guselkumab and tildrakizumab for the treatment of moderate to severe plaque psoriasis," J Dermatolog Treat., Sep. 2018, 29(6):569-578.
Bissonnette et al., "A randomized, double-blind, placebo-controlled, dose-escalation study of the safety and efficacy of INCB039110, an oral janus kinase 1 inhibitor, in patients with stable, chronic plaque psoriasis," J Dermatolog Treat., Jan. 14, 2016, 27(4):332-338.
Calautti et al., "Psoriasis: A STAT3-Centric View ," Int J Mol Sci., Jan. 2018, 19(1):171.
D'Amico et al., "Janus kinase inhibitors for the treatment of inflammatory bowel diseases: developments from phase I and phase II clinical trials," Expert Opinion on Investigational Drugs, 2018, 27(7):595-599.
Fuss et al., "Nonclassical CD1d-restricted NK T cells that produce IL-13 characterize an atypical Th2 response in ulcerative colitis," The Journal of Clinical Invetsigation, May 2004, 113(10):1490-1497.
Gerlach et al., "TH9 cells that express the transcription factor PU.1 drive T cell-mediated colitis via IL-9 receptor signaling in intestinal epithelial cells," Nature Immunology, Jul. 2014, 15(7):676-686.

(Continued)

Primary Examiner — Charanjit Aulakh
(74) Attorney, Agent, or Firm — Fish & Richardson P.C.

(57) ABSTRACT

This disclosure relates to JAK1 pathway inhibitors and the use thereof in treating gastrointestinal diseases or disorders such as ulcerative colitis.

18 Claims, 18 Drawing Sheets

(56) References Cited

OTHER PUBLICATIONS

Heinrich et al., "Principles of interleukin (IL)-6-type cytokine signalling and its regulation," The Biochemical Journal, 2003, 374(Pt 1):1-20.

Hirota et al., "T cell self-reactivity forms a cytokine milieu for spontaneous development of IL-17+ Th cells that cause autoimmune arthritis," J Exp Med., Jan. 22, 2007, 204(1):41-47.

International Search Report and Written Opinion in International Application No. PCT/US2019/067418, dated Mar. 17, 2020, 12 pages.

Isomäki et al., "The activity of JAK-STAT pathways in rheumatoid arthritis: constitutive activation of STAT3 correlates with interleukin 6 levels," Rheumatology, Jun. 1, 2015, 54(6):1103-1113.

Kojima et al., "Oxazolone-Induced Colitis in BALB/C Mice: a New Method to Evaluate the Efficacy of Therapeutic Agents for Ulcerative Colitis," J Pharmacol Sci., 2004, 96(3):307-313.

Loftus et al., "Clinical epidemiology of inflammatory bowel disease: Incidence, prevalence, and environmental influences," Gastroenterology 2004, 126(6):1504-1517.

Mascarenhas et al., "Primary analysis of a phase II open-label trial of INCB039110, a selective JAK1 inhibitor, in patients with myelofibrosis," Haematolgica, Feb. 2017, 102(2):327-335.

Narazaki et al., "The role and therapeutic targeting of IL-6 in rheumatoid arthritis," Expert Rev Clin Immunol., Jun. 2017, 13(6):535-551.

No Author, "Ulcerative Colitis: Clinical Trial Endpoints: Guidance for Industry," Food and Drug Administration, 2016, retrieved from URL <https://www.fda.gov/downloads/Drugs/GuidanceComplianceRegulatoryInformation/Guidances/UCM515143.pdf>, 22 pages.

Park et al., "Homogeneous proximity tyrosine kinase assays: scintillation proximity assay versus homogeneous time-resolved fluorescence," Analytical Biochemistry, 1999, 269(1):94-104.

Parmentier et al., "In vitro and in vivo characterization of the JAK1 selectivity of upadacitinib (ABT-494)," BMC Rheumatology, 2018, 2:23.

Randhawa et al., "A Review on Chemical-Induced Inflammatory Bowel Disease Models in Rodents," J Physiol Pharmacol., Aug. 2014, 18(4):279-288.

Remington's Pharmaceutical Sciences, 17th Ed., (Mack Publishing Company, Easton, 1985), p. 1418.

Sandborn et al., "Tofacitinib as Induction and Maintenance Therapy for Ulcerative Colitis," N Engl J Med., 2017, 376(18):1723-1736.

Sandborn et al., "Tofacitinib, an Oral Janus Kinase Inhibitor, in Active Ulcerative Colitis," The New England Journal of Medicine, Jul. 31, 2012, 367(7):616-624.

Solberg et al., "Clinical course during the first 10 years of ulcerative colitis: results from a population-based inception cohort (IBSEN Study)," Scand J Gastroenterol., 2009, 44:431-440.

Vermeire et al., "Clinical remission in patients with moderate-to-severe Crohn's disease treated with filgotinib (the FITZROY study): results from a phase 2, double-blind, randomised, placebo-controlled trial," Lancet, 2017, 389:266-275.

Zhou et al., "IL-6 programs T(H)-17 cell differentiation by promoting sequential engagement of the IL-21 and IL-23 pathways," Nat Immunol., Jun. 20, 2007, 8(9):967-974.

International Preliminary Report on Patentability in International Application No. PCT/US2019/067418, dated Jun. 16, 2021, 6 pages.

Adis R&D Profile, "Tofacitinib," Drugs in R & D., 2010, 10(4):271-284.

Changelian et al., "Prevention of Organ Allograft Rejection by a Specific Janus Kinase 3 Inhibitor," Science, Oct. 31, 2003, 302(5646):875-878.

Covington et al., "Preclinical characterization of itacitinib (INCB039110), a novel selective inhibitor of JAK1, for the treatment of inflammatory diseases," European Journal of Pharmacology, Oct. 15, 2020, 885:173505, 13 pages.

* cited by examiner

HS: Healthy subject; Grp: Group; Sub: Subject; QARL: Quantitative autoradioluminography;
UC: Ulcerative colitis.

7A

7B

7C

7D

11A: oral

11B: intracolonic

11C: oral (30 mg kg$^{-1}$)

11D: intracolonic (3 mg kg$^{-1}$)

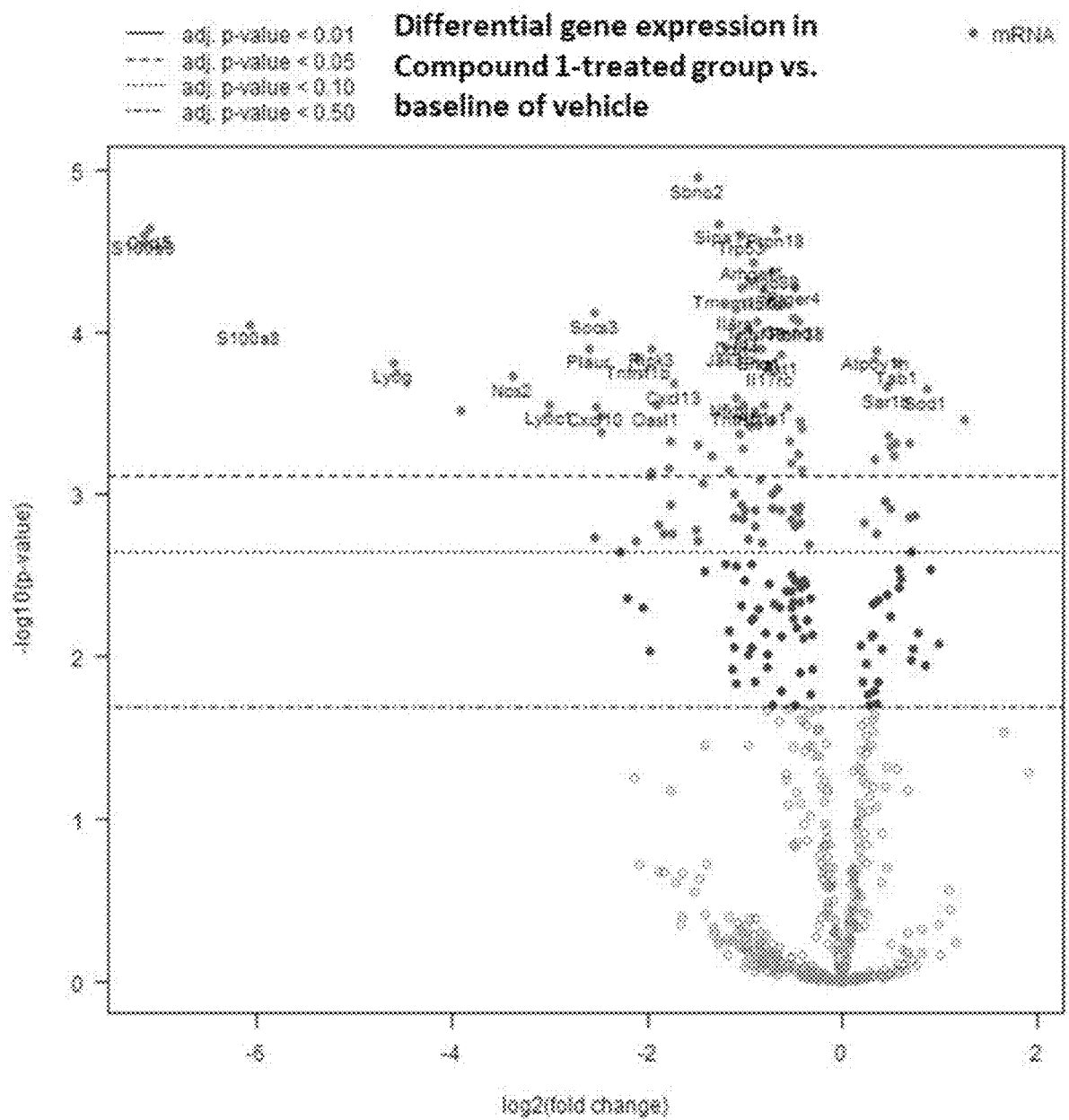

FIG. 12B

| Main Role | Gene Target | Log2 Fold Change | P-value |
|---|---|---|---|
| Chemokine signaling | Cxcl5 | -7.11 | 2.27E-05 |
| | Cxcl10 | -2.53 | 0.000287 |
| | Ccl5 | -1.76 | 0.000474 |
| | Cxcl9 | -2.55 | 0.00182 |
| Toll-like receptor signaling | IL1b | -3.91 | 0.000306 |
| | Nos2 | -3.37 | 0.000186 |
| | Ripk3 | -1.96 | 0.000126 |
| | Nfkbia | -1.08 | 0.000252 |
| JAK/STAT pathway | Socs3 | -2.54 | 7.62E-05 |
| | Socs1 | -2.47 | 0.000326 |
| | Jak3 | -1.19 | 0.000123 |
| | STAT1 | -0.953 | 0.00976 |
| | il6 | -0.953 | 0.00976 |
| Neutrophil marker | Ly6g | -4.61 | 0.000157 |
| Monocyte marker | Ly6c1 | -3.01 | 0.00028 |

13A. Oral

13B. Intracolonic

14A. Vehicle Oral

14B. Compound 1, 30 mg/kg Oral

14C. Vehicle Intracolonic

14D. Compound 1, 3 mg/kg Intracolonic

JAK1 PATHWAY INHIBITORS FOR THE TREATMENT OF GASTROINTESTINAL DISEASE

TECHNICAL FIELD

This disclosure relates to JAK1 pathway inhibitors and the use thereof in treating gastrointestinal diseases or disorders.

BACKGROUND

Ulcerative colitis (UC) is the most common form of inflammatory bowel disease worldwide. It is a chronic, idiopathic, relapsing disease of the mucosa, which typically involves the rectum and extends proximally to involve the colon, resulting in diffuse friability and erosions with bleeding. There is some correlation between disease extent and symptom severity; however, the course of disease is mild in many patients (Solberg et al., Scand. J. Gastroenterol. 2009; 44:431-440). In most patients, the disease is characterized by periods of symptomatic flare-ups and remissions, and patients may also experience disease extension over time.

Patients with UC typically experience recurrent episodes of rectal bleeding and diarrhea, often associated with crampy abdominal pain and tenesmus. The hallmark clinical presentations include diarrhea, rectal bleeding, passage of mucus, tenesmus, urgency, and abdominal pain. Patients may also experience fatigue, fevers, weight loss, and dehydration, particularly in more severe cases. Mortality is not increased in UC in general but the disease may present as life-threatening fulminant colitis. Most patients follow a chronic intermittent course with periods of increased disease activity separated by periods of disease remission. After the initial diagnosis, approximately half of patients will have active disease at any single point in time and approximately 90% will have a disease course characterized by intermittent flares.

The incidence of UC in developing countries has been steadily increasing since the mid-20th century. The annual incidence of UC is 1.2 to 20.3 cases per 100,000 people with the highest incidence seen in populations in Northern Europe and North America (Loftus et al. Gastroenterology 2004; 126:1504-1517). The typical onset for UC occurs between 15 and 30 years of age (Andres et al., Gastroenterol. Clin. North Am. 1999; 28:255-281). Males and females appear to be affected in equal proportions. A westernized environment and lifestyle are recognized as risk factors for inflammatory bowel disease.

Current therapies for UC include mesalamine, glucocorticoids, thiopurines, and inhibitors of TNFα and α4β7 integrin. Many patients do not have a response to these therapies or have a response that is not sustained.

Despite these treatment options, a significant proportion of UC patients still require colectomy for refractory, severe fulminant disease, or, in some cases, for cancer prevention. Although patients with UC are often considered to be cured by colectomy and restorative proctocolectomy, the quality of life may be poor and the surgery can be associated with short-term and long-term complications, including decreased female fecundity and the development of pouchitis.

At present, no current pharmacological therapy is able to provide a cure for UC. The primary treatment goal is to induce remission and then to maintain that state.

Accordingly, there is a need to develop new therapies for the treatment of gastrointestinal diseases or disorders, such as ulcerative colitis. This application addresses this need and others.

DESCRIPTION OF THE DRAWINGS

FIG. 12A shows a volcano plot of differentially expressed genes in the IL-10 KO mouse colon following oral administration of Compound 1 in the spontaneous colitis mouse model.

FIG. 12B shows statistically significant differentially expressed genes in the Compound 1-treated mice compared to the vehicle group in the spontaneous colitis mouse model.

FIG. 15A shows representative colons and FIG. 15B shows hematoxylin/eosin stained colon sections. White arrows in FIG. 15B indicate areas of mononuclear cell infiltrates. 20× magnification, bar=100 μm.

SUMMARY

Figure 1:
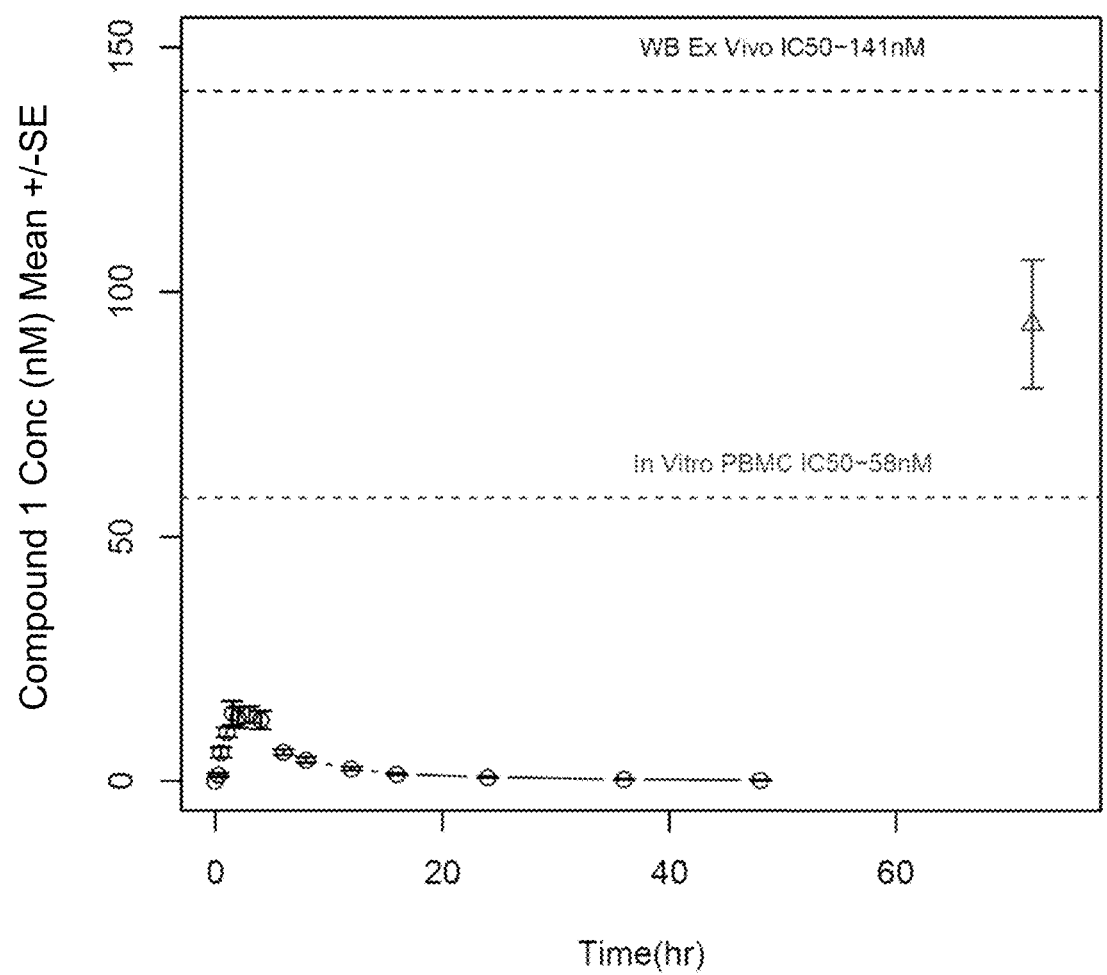
FIG. 1 depicts the mean plasma concentration-time profiles for the mean of the individual maximal fecal concentration following administration of Compound 1 at a 25 mg single dose.

Provided herein are methods for the treatment of a gastrointestinal disease or disorder in a subject in need thereof, comprising administering to said subject a therapeutically effective amount of a JAK1 pathway inhibitor, or a pharmaceutically acceptable salt thereof.

Provided herein is a JAK1 pathway inhibitor for the treatment of a gastrointestinal disease or disorder in a subject in need thereof.

Provided herein is a use of a JAK1 pathway inhibitor for manufacture of a medicament for use in treating a gastrointestinal disease or disorder in a subject in need thereof.

DETAILED DESCRIPTION

The present invention provides, inter alia, a method for treating a gastrointestinal disease or disorder in a subject in need thereof, comprising administering to said subject a therapeutically effective amount of a JAK1 pathway inhibitor, or a pharmaceutically acceptable salt thereof.

The methods described herein utilize JAK1 pathway inhibitors, particularly JAK1 selective inhibitors. A JAK1 selective inhibitor is a compound that inhibits JAK1 activity preferentially over other Janus kinases. JAK1 plays a central role in a number of cytokine and growth factor signaling pathways that, when dysregulated, can result in or contribute to disease states. JAK1 has been shown to cooperate with other JAKs to mediate the signaling of a number of inflammatory cytokines associated with many inflammatory disorders, including ulcerative colitis (UC). Inhibition of JAK/STAT signaling, by targeting multiple UC-associated cytokine pathways, has the potential to simultaneously reduce inflammation, cellular activation, and proliferation of key immune cells and therefore represents a promising therapeutic strategy for the treatment of UC. Tofacitinib for the treatment of UC was recently approved by the FDA. However, as a systemically acting, pan JAK inhibitor, tofacitinib therapy appears to carry an increased risk of immunosuppression (Sandborn et al., *N. Engl. J. Med.* 2017; 376: 1723-1736).

A JAK1 pathway inhibitor, specifically Compound 1 (i.e., {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, see Table 1), when administered in a sustained release form and at doses that are lower than that used for systemic therapy, maximizes colonic exposure while minimizing systemic exposure (see, e.g., Example 1). As a result, the efficacy of the JAK1 pathway inhibitor is expected to be mediated through predominantly local, rather than systemic, JAK1 inhibition.

Further, patients with gastrointestinal diseases may benefit from JAK1 inhibition, particularly selective JAK1 pathway inhibition. Selective inhibitors of JAK1 may be efficacious while avoiding unnecessary and potentially undesirable effects of inhibiting other JAK kinases.

Accordingly, provided herein are methods for treating a gastrointestinal related disease or disorder in a subject, said method comprising administering to the subject a JAK1 pathway inhibitor, or a pharmaceutically acceptable salt thereof, wherein the maximum fecal concentration of the JAK1 pathway inhibitor after administering the JAK1 pathway inhibitor is greater than or equal to about 25 nM; and the maximum total plasma concentration ($C_{max}$) after administering the JAK1 pathway inhibitor is less than or equal to about 450 nM.

Maximum fecal concentration can be determined by measuring fecal concentration using, for example, Liquid Chromatography with tandem Mass Spectrometry (LC-MS/MS) analysis over a period of time after administration of the JAK1 pathway inhibitor (e.g., from 0 to about 48 hours after administration of the JAK1 pathway inhibitor). Measuring the fecal concentration of Compound 1 can be carried out by the method described in Example C herein.

In some embodiments, the maximum fecal concentration of the JAK1 pathway inhibitor is greater than or equal to about 25 nM, about 30 nM, about 35 nM, about 40 nM, about 45 nM, about 50 nM, about 55 nM, about 60 nM, about 65 nM, about 70 nM, about 75 nM, about 80 nM, about 85 nM, about 90 nM, about 95 nM, or about 100 nM after administration of the JAK1 pathway inhibitor. In some embodiments, the maximum fecal concentration of the JAK1 pathway inhibitor is greater than or equal to about 50 nM after administration of the JAK1 pathway inhibitor. In some embodiments, the maximum fecal concentration of the JAK1 pathway inhibitor is between about 25 nM and 100 nM after administration of the JAK1 pathway inhibitor.

Maximum total plasma concentration (i.e., $C_{max}$) can determined by measuring plasma concentration using, for example, Liquid Chromatography with tandem Mass Spectrometry (LC-MS/MS) analysis over a period of time after administration of the JAK1 pathway inhibitor (e.g., from 0 to about 48 hours after administration of the JAK1 pathway inhibitor). Measuring the plasma concentration of Compound 1 can be carried out by the method described in Example C herein.

In some embodiments, the maximum total plasma concentration of the JAK1 pathway inhibitor is less than or equal to about 450 nM, about 425 nM, about 400 nM, about 375 nM, about 350 nM, about 325 nM, about 300 nM, about 275 nM, about 250 nM, about 225 nM, about 200 nM, about 175 nM, about 150 nM, about 125 nM, about 100 nM, about 75 nM, or about 50 nM after administration of the JAK1 pathway inhibitor. In some embodiments, the maximum total plasma concentration of the JAK1 pathway inhibitor is less than or equal to about 150 nM after administration of the JAK1 pathway inhibitor. In some embodiments, the maximum total plasma concentration of the JAK1 pathway inhibitor is less than or equal to about 141 nM after administration of the JAK1 pathway inhibitor. In some embodiments, the maximum total plasma concentration of the JAK1 pathway inhibitor is less than or equal to about 100 nM after administration of the JAK1 pathway inhibitor. In some embodiments, the maximum total plasma concentration is between about 25 nM and 100 nM.

In some embodiments, the maximum unbound plasma concentration of the JAK1 pathway inhibitor is less than or equal to about 150 nM after administration of the JAK1 pathway inhibitor. Maximum unbound plasma concentration can be derived from the maximum total plasma concentration of the JAK1 pathway inhibitor (see, e.g., Example C) and the in vitro protein binding, which can be determined by equilibrium dialysis. In some embodiments, the maximum unbound plasma concentration of the JAK1 pathway inhibitor is less than or equal to about 150 nM, about 125 nM, about 100 nM, about 75 nM, about 50 nM, or about 25 nM after administration of the JAK1 pathway inhibitor. In some embodiments, the maximum unbound plasma concentration of the JAK1 pathway inhibitor is less than or equal to about 100 nM after administration of the JAK1 pathway inhibitor.

In some embodiments, the maximum unbound plasma concentration of the JAK1 pathway inhibitor is less than or equal to about 50 nM after administration of the JAK1 pathway inhibitor.

In some embodiments, the ratio of maximum unbound plasma concentration over maximum fecal concentration is less than or equal to about 6, about 5, about 4, about 3, about 2, or about 1. In some embodiments, the ratio of maximum unbound plasma concentration over maximum fecal concentration is less than or equal to about 2. In some embodiments, the ratio of maximum unbound plasma concentration over maximum fecal concentration is between about 1 and about 6.

In some embodiments of the methods provided herein, the gastrointestinal related disease or disorder is selected from ulcerative colitis, Crohn's disease, and celiac disease.

In some embodiments, the gastrointestinal disease is relapsed, refractory, or relapsed and refractory ulcerative colitis. In some embodiments, the subject failed to respond to a previously administered treatment for ulcerative colitis. In other embodiments, the subject is intolerant to a previously administered treatment for ulcerative colitis. In some embodiments, the previously administered treatment is selected from (a) oral corticosteroids, (b) AZA or 6-MP, or (c) a biologic therapy such as infliximab or adalimumab.

I. JAK1 Pathway Inhibitors

The methods described herein utilize JAK1 pathway inhibitors. In some embodiments, the JAK1 pathway inhibitor is selective for JAK1 over JAK2, JAK3, and TYK2 (i.e., a JAK1 selective inhibitor). For example, the compounds described herein, or a pharmaceutically acceptable salt thereof, preferentially inhibit JAK1 over one or more of JAK2, JAK3, and TYK2. In some embodiments, the compounds inhibit JAK1 preferentially over JAK2 (e.g., have a JAK2/JAK1 $IC_{50}$ ratio >1). In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring $IC_{50}$ at 1 mM ATP (e.g., see Example A).

In some embodiments, the JAK1 pathway inhibitor is a compound of Table 1, or a pharmaceutically acceptable salt thereof. The compounds in Table 1 are selective JAK1 inhibitors (i.e., JAK1 pathway inhibitors, which are selective over JAK2, JAK3, and TYK2). The $IC_{50}$ values obtained by the method of Example A at 1 mM ATP are shown in Table 1.

TABLE 1

| Comp. No. | Prep. | Name | Structure | JAK1 IC$_{50}$ (nM) | JAK2/JAK1 |
|---|---|---|---|---|---|
| 1 | US 2011/ 0224190 (Example 1) | {1-{1-[3-Fluoro-2-(trifluoromethyl)isonicoti-noyl]piperidin-4-yl}-3-[4-(7H-pyrrolo[2,3-d]pyrimidin-4-yl)-1H-pyrazol-1-yl]azetidin-3-yl}acetonitrile | 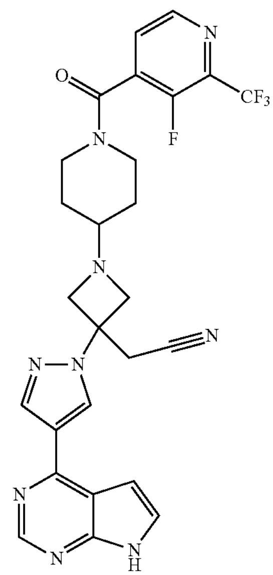 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 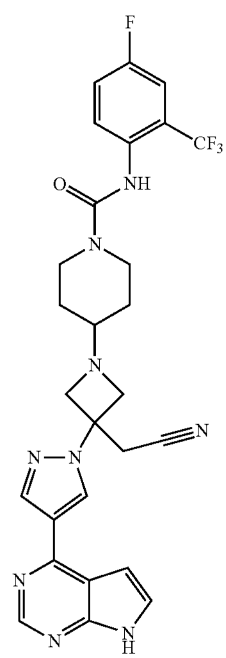 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 3 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 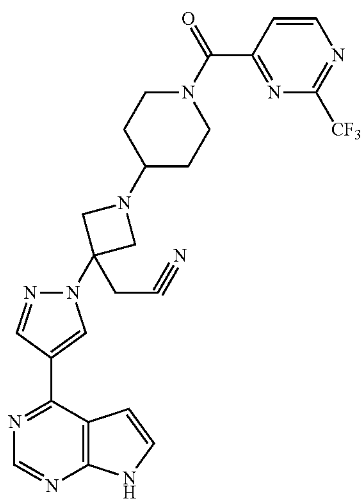 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 4 | US 2014/ 0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 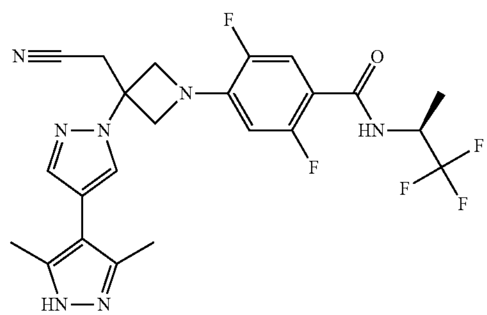 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 5 | US 2014/ 0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 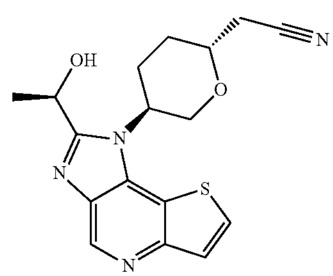 [SMILES: C[C@@H](O)c1nc2cnc3ccsc3c2n1[C@H]1CC[C@H](CC#N)OC1] | ++ | >10 |
| 6 | US 2010/ 0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 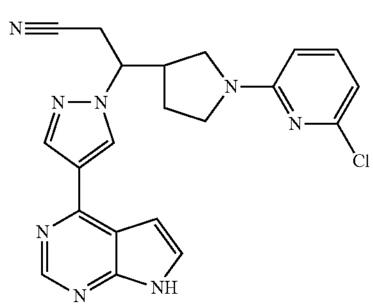 [SMILES: N#CCC(C1CCN(c2cccc(Cl)n2)C1)n1cc(-c2ncnc3[nH]ccc23)cn1] | + | >10 |

TABLE 1-continued

| Comp. No. | Prep. | Name | Structure | JAK1 IC$_{50}$ (nM) | JAK2/JAK1 |
|---|---|---|---|---|---|
| 7 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 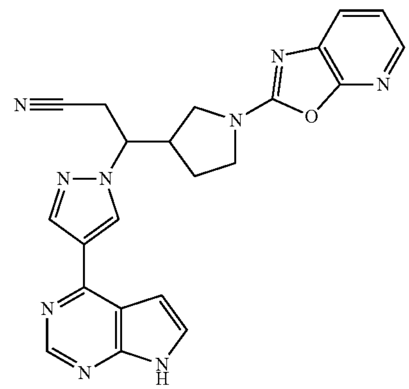 [SMILES: N#CCC(C1CCN(c2nc3cccnc3o2)C1)n1cc(-c2ncnc3[nH]ccc23)cn1] | + | >10 |
| 8 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 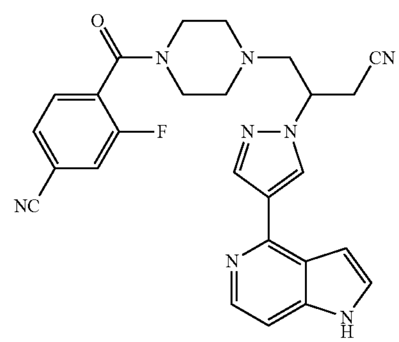 [SMILES: N#CCC(CN1CCN(C(=O)c2ccc(C#N)cc2F)CC1)n1cc(-c2nccc3[nH]ccc23)cn1] | + | >10 |
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 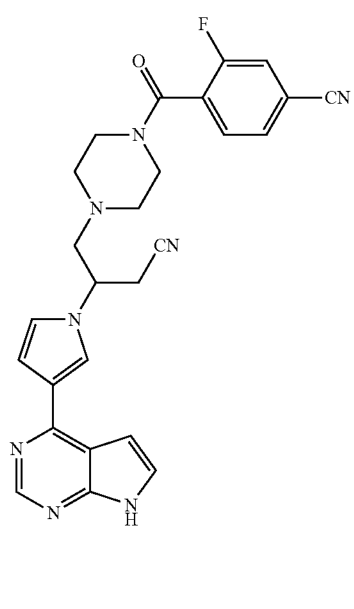 [SMILES: N#CCC(CN1CCN(C(=O)c2ccc(C#N)cc2F)CC1)n1ccc(-c2ncnc3[nH]ccc23)c1] | + | >10 |

TABLE 1-continued
| Comp. No. | Prep. | Name | Structure | JAK1 IC$_{50}$ (nM) | JAK2/ JAK1 |
|---|---|---|---|---|---|
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 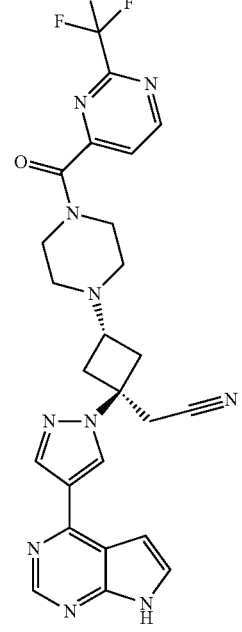 | + | >10 |
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 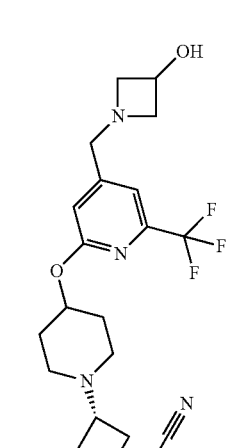 | + | >10 |

TABLE 1-continued

| Comp. No. | Prep. | Name | Structure | JAK1 IC$_{50}$ (nM) | JAK2/JAK1 |
|---|---|---|---|---|---|
| 12 | US 2012/0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-l)-1H-pyrazol-1-yl]cyclobutyl}acetonitrile | 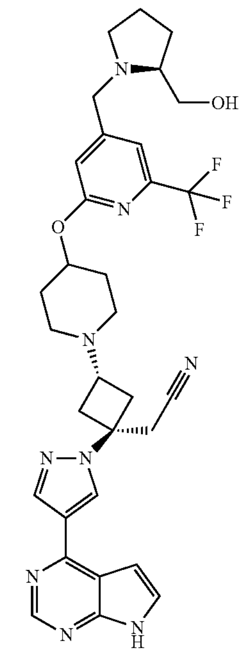 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 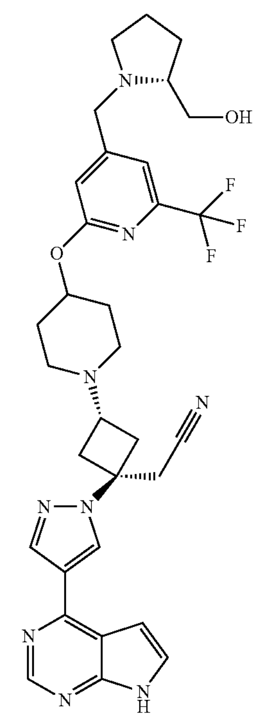 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 14 | US 2012/ 0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 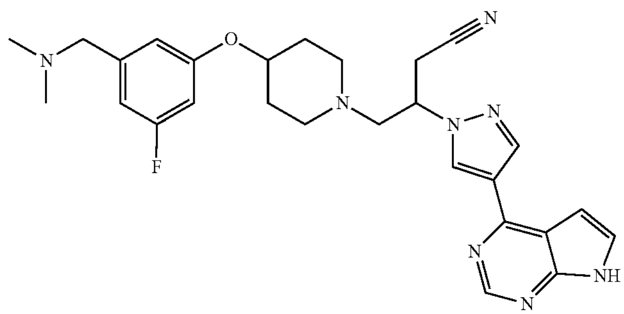 | + | >10 |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 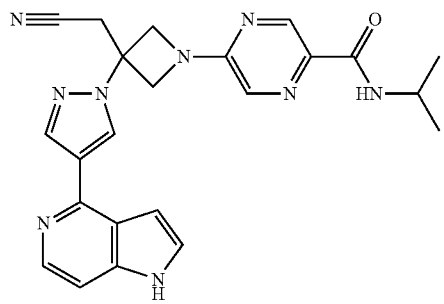 [SMILES: CC(C)NC(=O)c1cnc(N2CC(CC#N)(n3cc(-c4nccc5[nH]ccc45)cn3)C2)cn1] | + | >10 |
| 16 | US 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 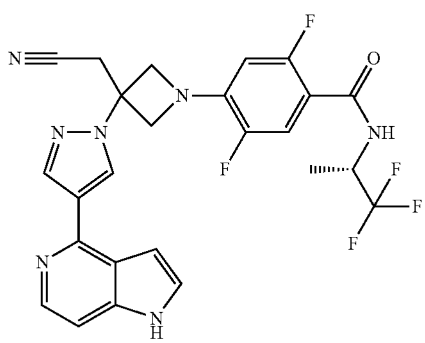 [SMILES: C[C@H](NC(=O)c1cc(F)c(N2CC(CC#N)(n3cc(-c4nccc5[nH]ccc45)cn3)C2)cc1F)C(F)(F)F] | + | >10 |
| 17 | US 2013/ 0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 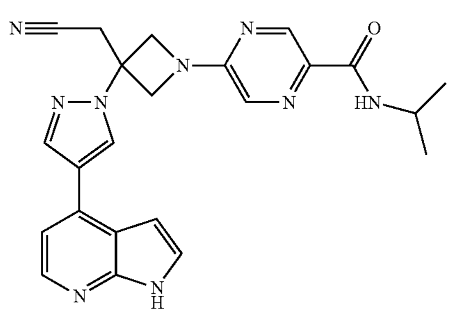 [SMILES: CC(C)NC(=O)c1cnc(N2CC(CC#N)(n3cc(-c4ccnc5[nH]ccc45)cn3)C2)cn1] | + | >10 |

TABLE 1-continued

| Comp. No. | Prep. | Name | Structure | JAK1 IC$_{50}$ (nM) | JAK2/ JAK1 |
|---|---|---|---|---|---|
| 18 | US 2013/ 0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 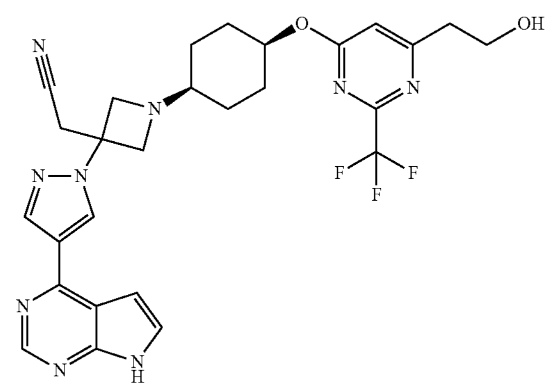 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/ 0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 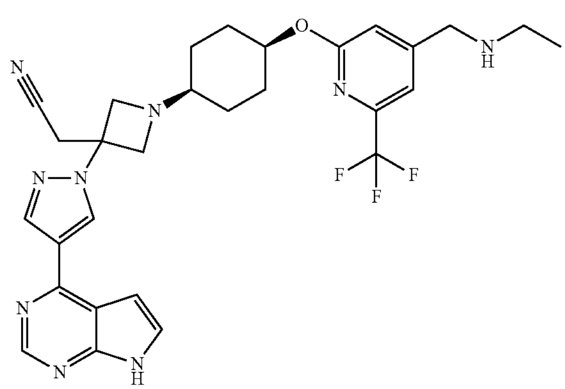 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/ 0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 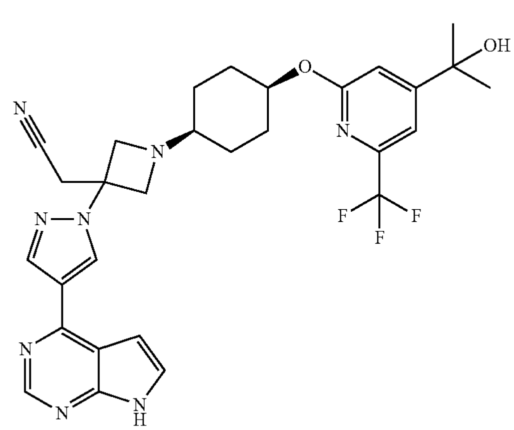 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 21 | US 2013/ 0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 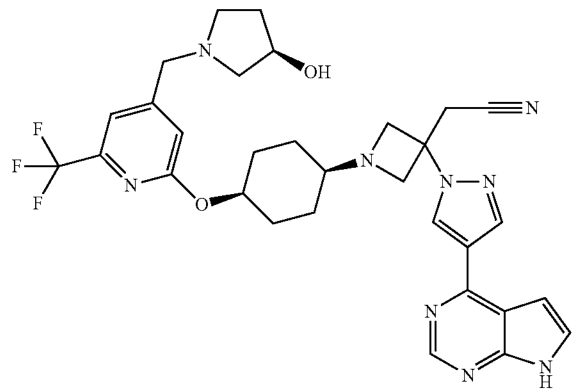 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 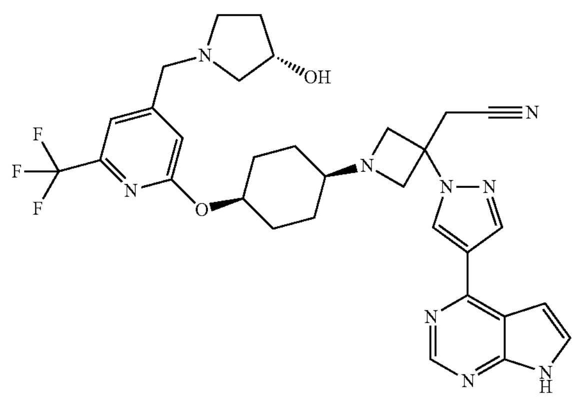 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | US 2014/ 0005166 (Example 1) | {trans-3-(4-{[4-{[(1S)-2-hydroxy-1-methylethyl)amino}methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 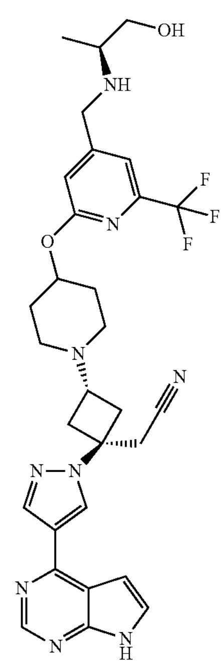 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 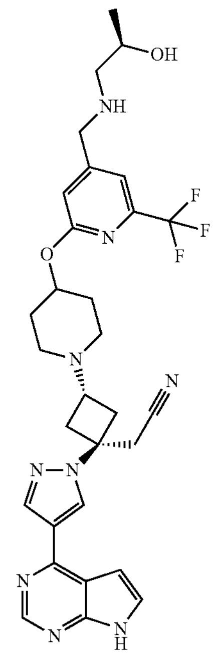 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 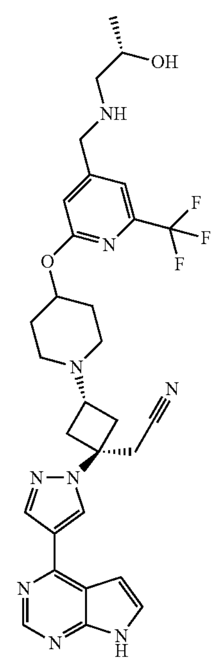 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 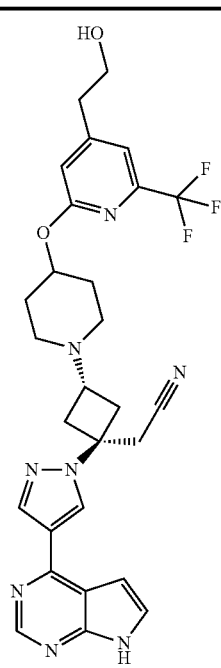 | + | >10 |

+ means <10 nM (see Example A for assay conditions)
++ means ≤100 nM (see Example A for assay conditions)
+++ means ≤300 nM (see Example A for assay conditions)
$^a$Data for enantiomer 1
$^b$Data for enantiomer 2

In some embodiments, the JAK1 pathway inhibitor is {1-{1-[3-fluoro-2-(trifluoromethyl)isonicotinoyl]piperidin-4-yl}-3[4-(7H-pyrrolo [2,3-d]pyrimidin-4-yl)-1H-pyrazol-1-yl]azetidin-3-yl}acetonitrile, or a pharmaceutically acceptable salt thereof.

In some embodiments, the JAK1 pathway inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H,1'H-4,4'-bipyrazol-1-yl)azetidin-1-yl]-2, 5-difluoro-N-[(1S)-2,2,2-trifluoro-1-methylethyl]benzamide and the phosphoric acid salt of the same can be found, e.g., in US Patent Publ. No. 2014/0343030, filed May 16, 2014, which is incorporated herein by reference in its entirety.

In some embodiments, the JAK1 pathway inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 1 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, JAK1 pathway inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK1 pathway inhibitor is a compound of Formula I

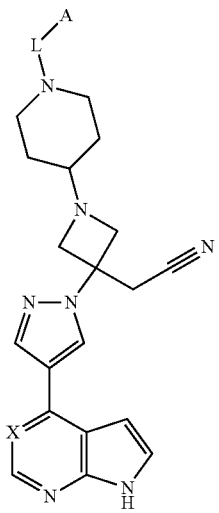

or a pharmaceutically acceptable salt thereof, wherein:

X is N or CH;

L is C(=O) or C(=O)NH;

A is phenyl, pyridinyl, or pyrimidinyl each of which is optionally substituted with 1 or 2 independently selected $R^1$ groups; and each $R^1$ is, independently, fluoro, or trifluoromethyl.

In some embodiments, the compound of Formula I is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the compound of Formula I is 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide, or a pharmaceutically acceptable salt thereof.

In some embodiments, the compound of Formula I is [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile, or a pharmaceutically acceptable salt thereof.

In some embodiments, the JAK1 pathway inhibitor is a compound of Formula II

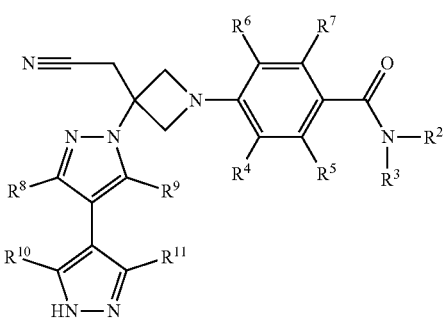

or a pharmaceutically acceptable salt thereof, wherein:

$R^2$ is $C_{1-6}$ alkyl, $C_{3-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^3$ is H or methyl;

$R^4$ is H, F, or Cl;

$R^5$ is H or F;

$R^6$ is H or F;

$R^7$ is H or F;

$R^8$ is H or methyl;

$R^9$ is H or methyl;

$R^{10}$ is H or methyl; and $R^{11}$ is H or methyl.

In some embodiments, the compound of Formula II is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 pathway inhibitor is a compound of Formula III

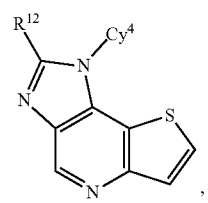

or a pharmaceutically acceptable salt thereof, wherein:

$Cy^4$ is a tetrahydro-2H-pyran ring, which is optionally substituted with 1 or 2 groups independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl; and $R^{12}$ is —$CH_2$—OH, —CH($CH_3$)—OH, or —$CH_2$—$NHSO_2CH_3$.

In some embodiments, the compound of Formula III is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor is administered in a daily amount of from about 1 mg to about 100 mg, about 3 mg to about 100 mg, about 5 mg to about 100 mg, about 10 mg to about 100 mg, about 10 mg to about 75 mg, or about 25 mg to about 75 mg on a free base basis.

In some embodiments, the JAK1 pathway inhibitor is administered in a daily amount of from about 1 mg to about 100 mg, from about 3 mg to about 100 mg, from about 5 mg to about 100 mg, from about 10 mg to about 100 mg, from about 10 mg to about 75 mg, or from about 25 mg to about 75 mg on a free base basis.

In some embodiments, the JAK1 pathway inhibitor is administered in a daily amount of from about 10 mg to about 100 mg on a free base basis. Accordingly, in some embodiments, the selective JAK1 pathway inhibitor is administered in a daily amount of about 1 mg, about 3 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg on a free base basis.

In some embodiment, the JAK1 pathway inhibitor, or pharmaceutically acceptable salt thereof, is administered at a daily dose of from about 50 mg to about 100 mg.

In some embodiments, the JAK1 pathway inhibitor, or pharmaceutically acceptable salt thereof, is administered at a daily dose of from about 25 mg to about 50 mg.

In some embodiments, the JAK1 pathway inhibitor, or pharmaceutically acceptable salt thereof, is administered at a daily dose of from about 25 mg to about 75 mg.

In some embodiments, the JAK1 pathway inhibitor, or pharmaceutically acceptable salt thereof, is administered at a daily dose of about 1 mg.

In some embodiments, the JAK1 pathway inhibitor, or pharmaceutically acceptable salt thereof, is administered at a daily dose of about 2 mg.

In some embodiments, the JAK1 pathway inhibitor, or pharmaceutically acceptable salt thereof, is administered at a daily dose of about 2.5 mg.

In some embodiments, the JAK1 pathway inhibitor, or pharmaceutically acceptable salt thereof, is administered at a daily dose of about 3 mg.

In some embodiments, the JAK1 pathway inhibitor, or pharmaceutically acceptable salt thereof, is administered at a daily dose of about 5 mg.

In some embodiments, the JAK1 pathway inhibitor, or pharmaceutically acceptable salt thereof, is administered at a daily dose of about 10 mg.

In some embodiments, the JAK1 pathway inhibitor, or pharmaceutically acceptable salt thereof, is administered at a daily dose of about 15 mg.

In some embodiments, the JAK1 pathway inhibitor, or pharmaceutically acceptable salt thereof, is administered at a daily dose of about 25 mg.

In some embodiments, the JAK1 pathway inhibitor, or pharmaceutically acceptable salt thereof, is administered at a daily dose of about 30 mg.

In some embodiments, the JAK1 pathway inhibitor, or pharmaceutically acceptable salt thereof, is administered at a daily dose of about 50 mg.

In some embodiments, the JAK1 pathway inhibitor, or pharmaceutically acceptable salt thereof, is administered at a daily dose of about 100 mg.

In some embodiments, the JAK1 pathway inhibitor, or pharmaceutically acceptable salt thereof, is administered once daily at a dose of about 25 mg.

In some embodiments, the JAK1 pathway inhibitor, or pharmaceutically acceptable salt thereof, is administered at a daily dose (e.g., as a once or twice-daily dose) of from about 1 mg/kg to about 50 mg/kg.

In some embodiments, the JAK1 pathway inhibitor, or pharmaceutically acceptable salt thereof, is administered at a daily dose (e.g., as a once or twice-daily dose) of from about 3 mg/kg to about 30 mg/kg.

In some embodiments, the JAK1 pathway inhibitor, or pharmaceutically acceptable salt thereof, is administered as a twice-daily (BID) dose of about 3 mg/kg for a total daily administration of about 6 mg/kg.

In some embodiments, the JAK1 pathway inhibitor, or pharmaceutically acceptable salt thereof, is administered as a twice-daily (BID) intracolonical dose of about 3 mg/kg for a total daily administration of about 6 mg/kg.

In some embodiments, the JAK1 pathway inhibitor, or pharmaceutically acceptable salt thereof, is administered as a twice-daily (BID) dose of about 30 mg/kg for a total daily administration of about 60 mg/kg.

In some embodiments, the JAK1 pathway inhibitor, or pharmaceutically acceptable salt thereof, is administered as a twice-daily (BID) oral dose of about 30 mg/kg for a total daily administration of about 60 mg/kg.

In some embodiments, the JAK1 pathway inhibitor, or pharmaceutically acceptable salt thereof, is administered twice daily at a dose of about 25 mg for a total daily administration of about 50 mg.

In some embodiments, the JAK1 pathway inhibitor, or pharmaceutically acceptable salt thereof, is administered once daily at a dose of about 50 mg.

In some embodiments, the JAK1 pathway inhibitor, or pharmaceutically acceptable salt thereof, is administered twice daily at a dose of about 50 mg for a total daily administration of about 100 mg.

In some embodiments, the JAK1 pathway inhibitor, or pharmaceutically acceptable salt thereof, is administered once daily at a dose of about 100 mg.

In some embodiments, the JAK1 pathway inhibitor, or pharmaceutically acceptable salt thereof, is administered as one or more sustained release dosage forms each comprising the JAK1 pathway inhibitor, or pharmaceutically acceptable salt thereof.

Provided herein is a method for treating a gastrointestinal disease in a subject, comprising administering to the subject a daily dose of from about 25 mg to 100 mg of a JAK1 pathway inhibitor, or a pharmaceutically acceptable salt thereof, wherein the JAK1 pathway inhibitor, or pharmaceutically acceptable salt thereof, is administered as one or more sustained release dosage forms comprising the JAK1 pathway inhibitor, or pharmaceutically acceptable salt thereof.

The embodiments described herein are intended to be combined in any suitable combination as if the embodiments are multiply dependent claims (e.g., the embodiments related to the selective JAK1 pathway inhibitor and doses of the same, the embodiments related to the maximum plasma concentration (total or unbound), the embodiments related to any salt forms of the compounds disclosed herein, the embodiments related to the individual types of gastrointestinal related diseases, and the embodiments related to composition and/or administration can be combined in any combination).

Also provided herein is a method for treating a gastrointestinal disease selected from the group consisting of inflammatory bowel disorder, ulcerative colitis, spontaneous colitis, Crohn's disease, and celiac disease. In some embodiments the gastrointestinal disease is selected from the group consisting of ulcerative colitis, Crohn's disease, and celiac disease.

In some embodiments, the gastrointestinal disease is selected from the group consisting of inflammatory bowel disorder, and spontaneous colitis.

In some embodiments, the gastrointestinal disease is spontaneous colitis.

For example, provided herein is a method for treating a gastrointestinal disease selected from the group consisting of ulcerative colitis, Crohn's disease and celiac disease, in a subject in need thereof, the method comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein the maximum fecal concentration of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile after administering {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or pharmaceutically acceptable salt thereof, is greater than about 25 nM, and wherein the maximum total plasma concentration of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile after administering {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or pharmaceutically acceptable salt thereof, is less than about 150 nM.

Also provided herein is a method for treating a gastrointestinal disease selected from the group consisting of ulcerative colitis, Crohn's disease and celiac disease, in a subject, the method comprising administering to the subject a once-daily dose of about 25 mg to about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein the dose comprises one or more sustained-release dosage forms each comprising the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

Also provided herein is a method for treating a gastrointestinal disease selected from the group consisting of ulcerative colitis, Crohn's disease and celiac disease, in a subject, the method comprising administering to the subject a twice-daily dose of about 25 mg on a free base basis of {1-{1-[3-fluoro-2-(trifluoromethyl)isonicotinoyl]piperidin-4-yl}-3-[4-(7H-pyrrolo [2,3-d]pyrimidin-4-yl)-1H-pyrazol-1-yl]azetidin-3-yl}acetonitrile, or a pharmaceutically acceptable salt thereof, wherein the dose comprises one or more sustained-release dosage forms each comprising the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

Also provided herein is a method for treating a gastrointestinal disease selected from the group consisting of ulcerative colitis, Crohn's disease and celiac disease, in a subject, the method comprising administering to the subject a twice-daily dose of about 50 mg on a free base basis of {1-{1-[3-fluoro-2-(trifluoromethyl)isonicotinoyl]piperidin-4-yl}-3-[4-(7H-pyrrolo [2,3-d]pyrimidin-4-yl)-1H-pyrazol-1-yl]azetidin-3-yl}acetonitrile, or a pharmaceutically acceptable salt thereof, wherein the dose comprises one or more sustained-release dosage forms each comprising the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

Sustained-release dosage forms of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof (Table 1, Compound 1) can be found in US Publ. No. 2015-0065484, filed Aug. 6, 2014, which is hereby incorporated by reference in its entirety. See also Example B infra.

All possible combinations are not separately listed herein merely for the sake of brevity.

The compounds described herein can be asymmetric (e.g., having one or more stereocenters). All stereoisomers, such as enantiomers and diastereomers, are intended unless otherwise indicated. Compounds that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formulae (I), (II), or (III) or a compound of Table 1 can be optionally substituted with deuterium atoms, such as —$CD_3$ being substituted for —$CH_3$).

The term, "compound," as used herein is meant to include all stereoisomers, geometric isomers, tautomers, and isotopes of the structures depicted, unless the name indicates a specific stereoisomer. Compounds herein identified by name or structure as one particular tautomeric form are intended to include other tautomeric forms unless otherwise specified.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The terms "individual," "patient," and "subject" are used interchangeably, and refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

Combination Therapies

The methods described herein can further comprise administering one or more additional therapeutic agents. These therapeutic agents include anti-inflammatory agents, steroids, immunosuppressants, or therapeutic anti-bodies.

For example, the methods described herein can be used in combination with current UC therapies such as oral mesalamine (5-ASA), oral corticosteroids, azathioprine (AZA), 6-mercaptopurine (6-MP), and methotrexate, infliximab, vedolizumab, mucosal addressin cell adhesion molecule (MADCAM1) inhibitors and fecal transplantation.

For example, oral 5-ASA (mesalamine, e.g., of from about 1600 mg/day to about 2400 mg/day) or sulfasalazine (up to e.g., of from about 1000 mg/day to 4000 mg/day) can be administered with the JAK1 pathway inhibitors for any of the methods described herein.

As another example, oral corticosteroids (e.g., of from about 0.5 mg/day to about 60 mg/day prednisone or oral corticosteroid equivalent) can be administered with the JAK1 pathway inhibitors for any of the methods described herein.

As another example, azathioprine of from about 50 mg/day to about 225 mg/day, 6-mercaptopurine up to, e.g., of from about 30 mg/day to about 112.5 mg/day, or methotrexate up to, e.g., about 25 mg weekly can also be administered with the JAK1 pathway inhibitors for any of the methods described herein. In some embodiments, azathioprine is administered at about 50 mg/day to about 100 mg/day with the JAK1 pathway inhibitors for any of the methods described herein. In other embodiments, 6-mercaptopurine is administered at from about 30 mg/day to about 50 mg/day with the JAK1 pathway inhibitors for any of the methods described herein.

As another example, a course of infliximab of 2-10 mg/kg for induction and maintenance, e.g., 5 mg/kg can be administered with the JAK1 pathway inhibitors for any of the methods described herein. In some embodiments, the infliximab is administered at 5 mg/kg at zero, two, and six weeks, then every eight weeks thereafter.

As another example, vedolizumab at doses of about 200 to about 400 mg, e.g., 300 mg, can be administered with the JAK1 pathway inhibitors for any of the methods described herein. In some embodiments, the vedolizumab is administered at zero, two, and six weeks, there every eight weeks thereafter.

When more than one pharmaceutical agent is administered to a subject, they can be administered simultaneously, sequentially, or in combination (e.g., for more than two agents).

Compositions

The compounds can be administered in the form of pharmaceutical compositions. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the administration is oral. In some embodiments, the administration is intracolonical.

The pharmaceutical compositions can contain, as the active ingredient, the compounds, or a pharmaceutically acceptable salt thereof, in combination with one or more pharmaceutically acceptable carriers (excipients). In some embodiments, the composition is suitable for topical administration. In making the compositions, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; and sweetening agents and flavoring agents. The compositions of the invention can be formulated so as to provide quick, sustained or delayed release of the active ingredient after administration to the patient by employing procedures known in the art.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

Kits

The present application also includes pharmaceutical kits useful, which include one or more containers containing a pharmaceutical composition comprising a therapeutically effective amount of the compound, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example A: In Vitro JAK Kinase Assay

JAK1 pathway inhibitors that can be used for the treatment of cytokine-related diseases or disorders are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag are expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds are measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 µL 45 mM EDTA, 300 nM SA-APC, 6 nM Eu-Py20 in assay buffer (Perkin Elmer, Boston, Mass.). Binding to the Europium labeled antibody takes place for 40 minutes and HTRF signal was measured on a Fusion plate reader (Perkin Elmer, Boston, Mass.). The compounds in Table 1 were tested in this assay and shown to have the $IC_{50}$ values in Table 1

Example B: Preparation of Sustained Release Formulations of Compound 1

Sustained release tablets comprising Compound 1 were prepared with the excipients being in the amounts shown in the tables below. Protocol A was used for the SR1 tablets, Protocol B was used for the SR2 tablets, Protocol C was used for the SR3 tablets and the 25 mg SR tablets, and Protocol D was used for the SR4 tablets. These procedures are disclosed in US Patent Publ. No. 2015/0065484, which is directed to sustained release dosage forms of Compound 1.

Protocol A:

Step 1. Individually screen the adipic acid salt of Compound 1, microcrystalline cellulose, hypromelloses (Methocel K100 LV and Methocel K4M), and lactose monohydrate.

Step 2. Transfer the screened material from Step 1 to a suitable blender and mix.

Step 3. Transfer the blend from Step 2 to a suitable granulator and mix.

Step 4. Add purified water while mixing.

Step 5. Transfer the granules from Step 4 into a suitable dryer and dry until LOD is less than 3%.

Step 6. Screen the granules from Step 5.
Step 7. Mix screened Magnesium Stearate with granules in Step 6 in a suitable blender.
Step 8. Compress the final blend in Step 7 on a suitable rotary tablet press.
Protocol B:
Step 1. Individually screen the adipic acid salt of the compound of Formula I, microcrystalline cellulose, hypromellose and pregelatinized starch.
Step 2. Transfer the screened material from Step 1 to a suitable blender and mix.
Step 3. Transfer the blend from Step 2 to a suitable granulator and mix.
Step 4. Add purified water while mixing.
Step 5. Transfer the granules from Step 4 into a suitable dryer and dry until LOD is less than 3%.
Step 6. Screen the granules from Step 5.
Step 7. Individually screened polyox, butylated hydroxytoluene and colloidal silicone dioxide.
Step 8. Transfer the granules from Step 6 and material from Step 7 into a suitable blender and mix.
Step 9. Add screened Magnesium Stearate to the material in Step 8 and continue blending.
Step 10. Compress the final blend in Step 9 on a suitable rotary tablet press.
Protocol C:
Step 1. Individually screen lactose monohydrate, the adipic acid salt of the compound of Formula I, microcrystalline cellulose and hypromelloses through a suitable screen.
Step 2. Transfer the screened material from Step 1 to a suitable blender and mix.
Step 3. Transfer the blend from Step 2 to a suitable granulator and mix.
Step 4. Add purified water while mixing.
Step 5. Screen wet granules through a suitable screen.
Step 6. Transfer the granules from Step 5 into a suitable dryer and dry until LOD is less than 3%.
Step 7. Mill the granules from Step 6.
Step 8. Mix screened magnesium stearate with granules in Step 7 in a suitable blender.
Step 9. Compress the final blend in Step 8 on a suitable rotary tablet press.
Protocol D:
Step 1. Individually screen pregelatinized starch, the adipic acid salt of the compound of Formula I, hypromellose, and a portion of required microcrystalline cellulose through a suitable screen.
Step 2. Transfer the screened material from Step 1 to a suitable blender and mix.
Step 3. Transfer the blend from Step 2 to a suitable granulator and mix.
Step 4. Add purified water while mixing.
Step 5. Screen wet granules through a suitable screen.
Step 6. Transfer the granules from Step 5 into a suitable dryer and dry until LOD is less than 3%.
Step 7. Mill the granules from Step 6.
Step 8. Screen the remaining portion of microcrystalline cellulose and half of the sodium bicarbonate.
Step 9. Transfer the milled granules from Step 7 and screened materials from Step 8 into a suitable blender and mix.
Step 10. Screen the remaining portion of sodium bicarbonate and mix with blend in Step 9.
Step 11. Screen magnesium stearate and mix with blend in Step 10.
Step 12. Compress the final blend in Step 11 on a suitable rotary tablet press.

SR1: Composition of 100 mg Sustained Release Tablets

| Component | Function | Weight (mg/tablet) | Composition (wt %) |
| --- | --- | --- | --- |
| Adipic acid salt of the Compound 1 [a] | Active | 126.42[a] | 21.1 |
| Microcrystalline Cellulose | Filler | 60.0 | 10.0 |
| Hypromellose (Methocel K100LV) | Release Control | 60.0 | 10.0 |
| Hypromellose (Methocel K4M) | Release Control | 60.0 | 10.0 |
| Lactose Monohydrate | Filler | 290.58 | 48.4 |
| Magnesium Stearate[b] | Lubricant | 3.0 | 0.5 |
| Purified Water[c] | Granulating Liquid | q.s. | — |
| Total | | 600.0 | 100 |

[a] Conversion factor for adipate salt to free base is 0.7911
[b] Added after granulation
[c] Removed during processing SR2: Composition of 100 mg Sustained Release Tablets

| Component | Function | Weight (mg/tablet) | Composition (wt %) |
| --- | --- | --- | --- |
| Adipic acid salt of Compound 1[a] | Active | 126.4[a] | 21.1 |
| Microcrystalline Cellulose | Filler | 180.0 | 30.0 |
| Hypromellose (Methocel K100LV) | Binder | 6.0 | 1.0 |
| Polyethylene Oxide (Polyox WRS 1105)[b] | Release Control | 180.0 | 30.0 |
| Pregelatinized Starch | Filler | 101.6 | 16.9 |
| Colloidal Silicon Dioxide[b] | Glidant | 3.0 | 0.5 |
| Butylated Hydroxytoluene[b] | Antioxidant | 0.012 | 0.002 |
| Magnesium Stearate[b] | Lubricant | 3.0 | 0.5 |
| Purified Water[c] | Granulating Liquid | q.s. | — |
| Total | | 600.0 | 100.0 |

[a] Conversion factor for adipate salt to free base is 0.7911
[b] Added after granulation
[c] Removed during processing SR3 (100 mg): Composition of 100 mg Sustained Release Tablets

| Component | Function | Weight (mg/tablet) | Composition (wt %) |
| --- | --- | --- | --- |
| Adipic acid salt of Compound 1[a] | Active | 126.4[a] | 21.1 |
| Microcrystalline Cellulose | Filler | 108.0 | 18.0 |
| Hypromellose (Methocel K100LV) | Release Control | 42.0 | 7.0 |
| Hypromellose (Methocel K4M) | Release Control | 30.0 | 5.0 |
| Lactose Monohydrate | Filler | 290.6 | 48.4 |
| Magnesium Stearate[b] | Lubricant | 3.0 | 0.5 |
| Purified Water[c] | Granulating Liquid | q.s. | — |
| Total | | 600.0 | 100.0 |

[a] Conversion factor for adipate salt to free base is 0.7911
[b] Added after granulation
[c] Removed during processing SR4: Composition of 100 mg Sustained Release Tablets

| Excipient | Function | Weight (mg/tablet) | Composition (wt %) |
|---|---|---|---|
| Adipic acid salt of Compound 1[a] | Active | 126.4[a] | 21.1 |
| Microcrystalline Cellulose[d] | Filler | 104.6 | 17.4 |
| Hypromellose (Methocel K100LV) | Release Control | 210.0 | 35.0 |
| Pregelatinized Starch | Filler | 60.0 | 10.0 |
| Sodium Bicarbonate[b] | Gastric Floating Aid | 96.0 | 16.0 |
| Magnesium Stearate[b] | Lubricant | 3.0 | 0.5 |
| Purified Water[c] | Granulation Liquid | q.s. | — |
| Total | | 600.0 | 100.0 |

[a] Conversion factor for adipate salt to free base is 0.7911
[b] Added after granulation
[c] Removed during processing
[d] Partial added before and partial added after granulation 25 mg SR: Composition of 25 mg Sustained Release Tablets

| Component | Function | Weight (mg/tablet) | Composition (wt %) |
|---|---|---|---|
| Adipic acid salt of the compound of Formula I[a] | Active | 31.6[a] | 12.6 |
| Microcrystalline Cellulose | Filler | 105.0 | 42.0 |
| Hypromellose, (Methocel K100LV) | Release Control | 25.0 | 10.0 |
| Hypromellose, (Methocel K4M) | Release Control | 25.0 | 10.0 |
| Lactose Monohydrate | Filler | 62.15 | 24.9 |
| Magnesium Stearate[b] | Lubricant | 1.25 | 0.5 |
| Purified Water[c] | Granulating Liquid | q.s. | — |
| Total | | 250 | 100.0 |

[a] Conversion factor for adipate salt to free base is 0.7911
[b] Added after granulation
[c] Removed during processing Example C: Compound 1 Bioanalysis in Plasma and Feces Two different assays can be used to understand the functional activity of JAK1 inhibition. The first is a standard cell based assay and the other using whole blood. The former is conducted using human peripheral blood mononuclear cells (PBMC); briefly, the cells are stimulated with IL-6 to increase JAK1 activity, which is measured via phosphorylated STAT3. As increasing concentrations of Compound 1 are added, a corresponding decrease in phosphorylated STAT3 is observed. This assay is appropriate to assess JAK1 activity and/or the inhibitory activity of Compound 1 in samples that are devoid of serum proteins, e.g., feces samples.

To assess the inhibitory activity of Compound 1 in serum-rich media, e.g., plasma or whole blood, the assay is conducted using whole blood; briefly, the whole blood sample is stimulated with IL-6 and levels of phosphorylated STAT3 are determined. This assay can be conducted either in vitro (human blood samples are spiked with Compound 1) or ex vivo (whole blood samples collected from human subjects dosed with Compound 1).

I. Compound 1 in Human Plasma

The method used for analyzing Compound 1 in human plasma has been validated. Briefly, 50 µL of human plasma sample is placed in a 96-well plate. After an aliquot of 50 µL of internal standard (dissolved in 50:50 acetonitrile:water) is added, an aliquot of 100 µL of 0.1 M NaHCO3 is added. Then 800 µL of methyl-t-butyl ether (MtBE) is added and the samples are covered and vortexed. After centrifugation, 700 µL of MtBE layer is transferred to a clean 96-well plate. The samples are then dried under nitrogen at approximately 50° C. An aliquot of 250 µL of reconstitution solution (acetonitrile:water, 50:50, v/v) is then added to each sample. The plate is placed in the autosampler tray and injected into an LC-MS/MS for analysis. The LC-MS/MS analysis is carried out with an AB Sciex 4000 or a Sciex 6500 QTRAP mass spectrometer coupled with an HPLC pump and an autosampler. The chromatographic separation is achieved on a Waters T3 (50 mm×2.1 mm) HPLC column, with isocratic elution. The mass spectrometer is operated in positive ESI mode. The multiple reaction monitoring (MRM) transition is m/z 554.1→186.0 for Compound 1 and m/z 558.1→190.0 for the internal standard. Peak-area integrations are performed using the Analyst software and concentrations are calculated in Watson LIMS. Concentrations are calculated using 10 concentration levels ranging from 5 nM to 5000 nM with weighted linear regression, according to the following formula:

$$y = ax + b \text{(weighting factor} = 1/x^2\text{)}$$

where: x=Compound 1 concentration in nM; y=Peak-area ratio; a=Slope; and b=Intercept.

The lower limit of quantitation is 5 nM and the calibration curve ranges from 5 nM to 5000 nM for Compound 1 in human plasma.

II. Compound I in Human Feces

The method used for analyzing Compound 1 in human feces is a qualified method. The human fecal samples are collected in 1:1 homogenate at the clinical site [1 part of water (mL): 1 part of faces(g)]. Prior to sample analysis, additional water is added to the sample homogenate to achieve the final ratio of feces to water at 1:19 as calibration standard and QC samples. The final homogenates are processed and analyzed with calibration standards and QC samples. For human homogenate analysis, briefly, 100 µL of the feces homogenate (blanks, QC and study samples) is placed in a test tube. After an aliquot of 20 µL of internal standard is added and mixed, an aliquot of 200 µL of 0.1 M NaHCO3 is added and vortexed. Then 2 mL of MtBE is added and the samples are vortexed. After centrifugation, MtBE layer is transferred to a clean test tube. The samples were then dried under nitrogen at approximately 40° C. An aliquot of 1 mL of reconstitution solution (acetonitrile:water, 50:50, v/v) is then added to each sample and vortexed. Then 10 µL of the sample was diluted with 3 mL reconstitution solution in a clean test tube. The sample is transferred to an autosampler vial and 10 µL is injected into an LC-MS/MS for analysis. The LC-MS/MS analysis is carried out with an AB Sciex API 4000 or API 4000 QTrap mass spectrometer coupled with an HPLC pump and an autosampler. The chromatographic separation is achieved on a Agilent Eclipse Plus C8 50×4.6 mm, 5 µm HPLC column, with gradient elution. The mass spectrometer is operated in positive ESI mode. MRM transition is m/z 554.3→186.2 for Compound 1 and m/z 558.4→190.2 for the internal standard. Peak-area integrations are performed using the Analyst software and concentrations are calculated in Watson LIMS. Concentrations of human feces homogenates are calculated using 8 concentration levels ranging from 1 µg/g to 300 µg/g (1.8 µM to 542 µM) with weighted linear regression, according to the following formula:

$$y = ax + b \text{(weighting factor=1/}x^2\text{)}$$

where x=Compound 1 concentration in µg/g in human feces homogenates, y=Peak-area ratio, a=Slope, and b=Intercept.

Example 1: Dosing Strategy for Compound I, a Selective JAK1 Inhibitor, for the Treatment of Ulcerative Colitis Compound 1 is a JAK1 inhibitor currently under development for oncologic and auto-immune diseases. A clinical and an ex vivo study were conducted to understand colonic disposition, which is important for ulcerative colitis (UC).

Methods: Compound 1 concentrations in plasma and feces (colonic surrogate) were determined following a single sustained release 25 mg oral dose (see, e.g., Example B, 25 mg SR composition). Compound 1 concentrations in plasma following a single 100 mg dose were also determined in a separate study (see, e.g., Example C for measuring concentrations of Compound 1 in plasma). Ex vivo study: Colon tissue samples from healthy and UC subjects (2/group) were mounted on a vertical Ussing diffusion chamber. $[^{14}C]$ Compound 1 was applied to the apical side of the chamber at 100 and 1000 nM and incubated for 1 h. Samples were collected from the donor and receiver sides for determination of Compound 1 concentration. The colonic tissue was snap frozen for quantitative autoradiography.

Figure 2:
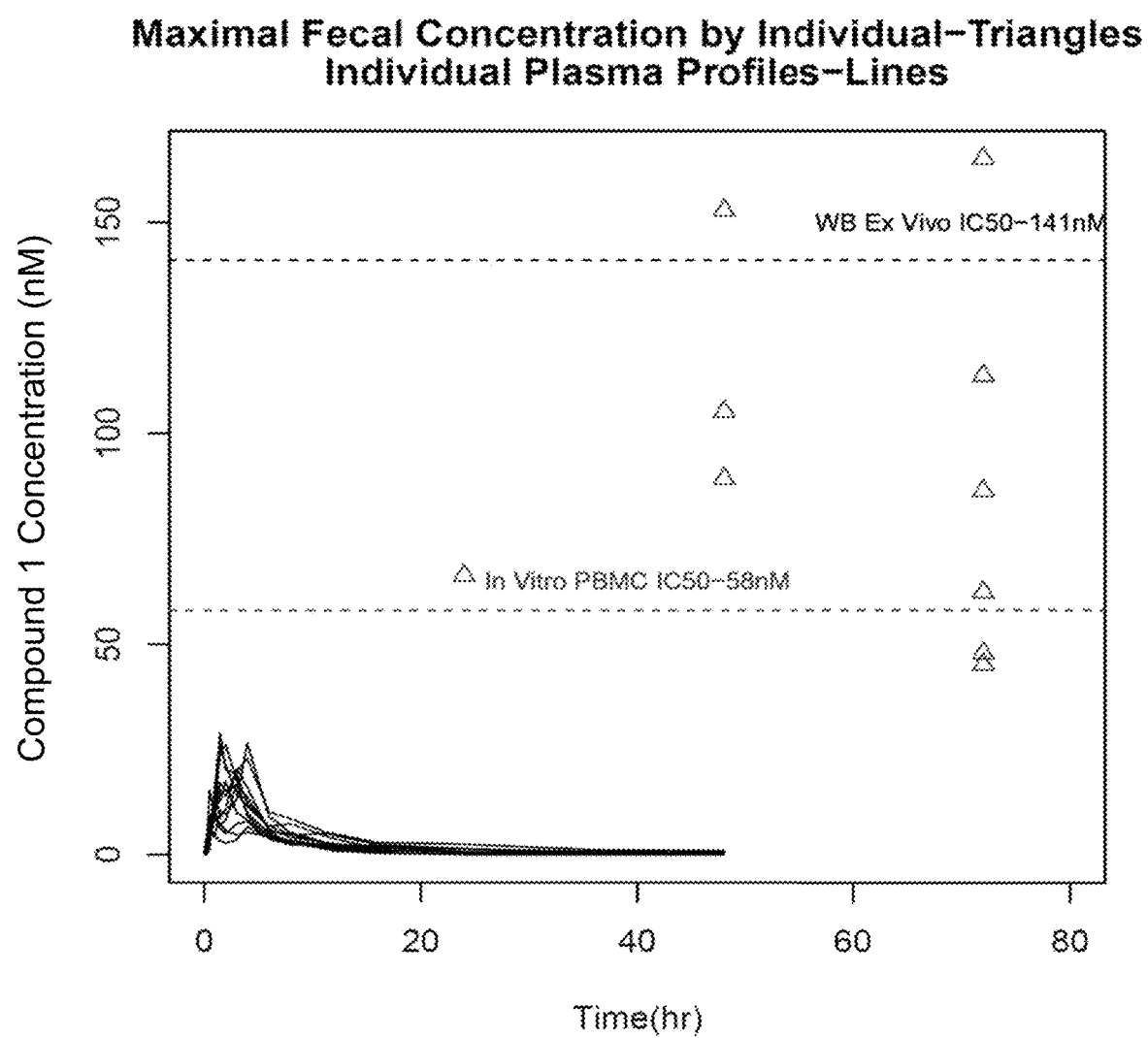
FIG. 2 depicts the individual plasma concentration-time profiles of fecal concentrations following administration of Compound 1 at a 25 mg single dose.

Results: Compound 1 is delivered as a sustained release formulation with 27.1% of the dose eliminated as unchanged Compound 1 in the feces (see, e.g., Example C for measuring concentrations of Compound 1 in feces). Following a single 25 mg dose of Compound 1, eight of twelve patients had maximum fecal concentrations that exceeded the in vitro $IC_{50}$ for JAK1 inhibition (i.e., 58 nM) (FIGS. 1 and 2). Maximal Fecal PK Mean (SD), GM=93.4 nM (41.4 nM), 85.5 nM, wherein PK is pharmacokinetic, SD is standard deviation, and GM is geometric mean. The maximum fecal concentration was taken directly from the observed fecal data, e.g. concentrations in feces collected from 0-24 hours.

Systemic concentrations were below the $IC_{50}$ for JAK1 inhibition in whole blood for either dose, mean (SD) $C_{max}$=18.9 (7.46) nM for 25 mg and 84.4 (45.8) nM for 100 mg (FIG. 1 and the table below).

| Variable | N | Mean | SD | Geometric Mean |
|---|---|---|---|---|
| $AUC_{all}$ (nM · hr) | 12 | 110 | 36.6 | 105 |
| $AUC_{0-inf}$ (nM · hr) | 12 | 117 | 38.7 | 111 |
| Cl/F (L/hr) | 12 | 424 | 131 | 405 |
| $C_{max}$ (nM) | 12 | 18.9 | 7.46 | 17.2 |
| Half-life or $t_{1/2}$ (hr) | 12 | 12.3 | 11.0 | 9.04 |
| $V_z/F$ (L) | 12 | 7360 | 6880 | 5290 |
| $T_{max}$ (hr) (median, min, max) | 12 | 2 | 1 | 4 |

Standard noncompartmental pharmacokinetic methods were used to analyze Compound 1 plasma concentrations. The $C_{max}$ (maximum plasma concentration) and $T_{max}$ (time at which the maximum plasma concentration occurs) were taken directly from the observed plasma concentration data. The terminal-phase disposition rate constant ($\lambda_z$) was estimated using a log-linear regression of the concentration data in the terminal disposition phase, and $t_{1/2}$ was estimated as $\ln(2)/\lambda_z$. $AUC_{all}$ is defined as the area under the plasma concentration-time curve from time 0 to the last observation calculated using the linear trapezoidal rule for increasing concentrations and logarithmic trapezoidal rule for decreasing concentrations. $AUC_{0-inf}$ was calculated as $AUC_{0-t} + C_t/\lambda_z$, where by $AUC_{0-t}$ is defined as the area under the plasma concentration-time curve from time 0 to the last measureable concentration (also calculated using the linear-up/log-down trapezoidal rule) and $C_t$ is the last measurable concentration. Cl/F is the apparent clearance and is calculated as Dose/$AUC_{0-inf}$. $V_z/F$ is the apparent volume of distribution based on the terminal phase calculated as Dose/($\lambda_z * AUC_{0-inf}$).

Ex vivo, no Compound 1 related radioactivity was detected from the receiver side. Compound 1 penetrated into the mucosal layer and, to a lesser extent, submucosal layer in a concentration dependent manner (See Example 2).

Summary: A dose range of about 25 mg to about 100 mg BID (twice daily) or about 25 mg to about 200 mg QD (once daily) is recommended for study in UC patients to maximize colonic exposure while minimizing the potential for systemic exposure.

Example 2: Tissue Penetration and Distribution Analysis of $[^{14}C]$Compound 1 in Colon from Healthy and Ulcerative Colitis Subjects by Microautoradiography (MARG) and Quantitative Autoradioluminography (QARL)

I. OBJECTIVES

The objectives of this study were to determine the tissue distribution of $[^{14}C]$Compound 1 related radioactivity in colon samples collected from healthy colon and ulcerative colitis (UC) human subjects using quantitative autoradioluminography (QARL) and microautoradiography (MARG).

II. MATERIALS AND METHODS

A. Sample Submission

A small piece of two colon samples from two healthy and UC subjects (total eight samples) were provided by Analytical Biological Services Inc. (Wilmington, Del.) and stored at −70° C. until use.

B. Dose Formulation

Dose formulations, i.e., 100 nM and 1000 nM, were prepared on the day of the experiment for all tissues in the study. $[^{14}C]$Compound 1 (1.06 mg) was dissolved in dimethyl sulfoxide (DMSO; 1.514 mL) to produce a 1 mM stock solution (0.7 mg/mL). The stock solution (20 µL) was diluted with Krebs-Ringer bicarbonate (KRB) buffer (20 mL) to reach the final concentrations of 1000 nM. 1000 nM dose formulation (2 mL) was diluted with KRB buffer (18 mL) to reach the final concentrations of 100 nM. The pH of both dose formulations were approximately 5.5.

The dose formulation was analyzed prior to incubation, to determine the radioactivity concentration and homogeneity. A 100 µL aliquot was taken from the top, middle, and bottom of the formulation container, and each was weighed and diluted to 10 mL with DMSO for radioactivity analysis. Triplicate aliquots of each 10 mL dilution were analyzed by liquid scintillation counting (LSC).

C. Incubation and Sample Collections

Intestinal tissue permeation studies were performed using a vertical Ussing diffusion chamber system (Harvard Apparatus, Holliston, Mass.) for healthy tissues. Frozen tissues were thawed to ambient temperature and rinsed with prewarmed KRB buffer used for dose formulation before being gently placed on the apparatus. Permeation was carried out mucosal-to-serosal at 37° C. for 1 hour with test article in KRB buffer added to the mucosal side. The receiver side of Ussing chamber containing blank KRB buffer was stirred with air bubbles by an aerator. Due to the limited availability of the samples, UC tissues were mounted (mucosal side up) on one end of a polypropylene tube with both ends cut open, and serosal side placed on blank KRB buffer in a vial with a stirring bar. KRB containing the test article was added into the tube and thus the mucosal side of the tissue was exposed to test article during the incubation. After 1 hour incubation at 37° C., samples (100-500 μL) were taken from both donor and receiver side, and then transferred to a 1.5 mL tube for evaluating the permeation. Tissue samples were gently removed from the chamber (healthy tissue) or the tube (UC tissue) and snap-frozen into liquid nitrogen-cooled isopentane for approximately 30 seconds. The individual frozen healthy and UC colon samples were embedded in Cryogel media, with the larger healthy tissues samples divided in ½ for a primary sample and a secondary sample.

D. Sample Analysis

[$^{14}$C]Compound 1 concentrations in both donor and receiver sides were analyzed by LSC. The lower limit of quantitation (LLOQ) was determined as 2 times the background (21 dpm).

The tissue samples were mounted for sectioning in a manner that would allow the tissues to be sectioned in cross section, from mucosal to serosal layers represented in each section.

Samples were cryo-sectioned at 40 μm (for QARL) and at 6-8 μm (for MARG) at approximately −20° C. and were collected onto glass microscope slides by thaw-mounting followed by heat fixation on a slide warmer. Approximately 3 tissue sections were obtained from each sample for QARL. After QARL sectioning, approximately 10 sets of 3 sections/slide were obtained for MARG.

E. QARL

The slides with 40 μm sections were mounted on cardboard backing, covered with plastic wrap, and were co-exposed to phosphorimaging screens along with [14C] spiked blood calibration standards (10 concentrations in triplicate that ranged from 0.00030 μCi/g to 7.72 μCi/g). The imaging plate, sections, and calibration standards were placed in a light-tight exposure cassette, in a copper lined lead safe, for a 4-day exposure at room temperature. The imaging plate was scanned using the Typhoon FLA 9500 image acquisition system (GE Healthcare, Sunnyvale, Calif.) and the resultant image stored on a dedicated QPS computer server. Images produced by the [14C]-spiked blood calibration standards were used to produce an image calibration curve using image analysis software (Micro-Computer Imaging Device (MCID Image Analysis System, Interfocus Imaging, Cambridge, Linton, UK).

F. MARG

All tissue sections were thaw mounted onto subbed glass microscope slides that were pre-coated with photographic emulsion in the dark and heat-fixed on a slide warmer. Slides were then placed in black slide boxes containing desiccant. The slide box was taped with black electrical tape and placed into a lead-lined container at 4° C. Slides were exposed to the photographic emulsion for 72 h, 1 week, 10 days, 2 weeks, 4 weeks, 6 weeks, and 8 weeks. The slides were developed with Kodak D19 Replacement developer and Kodak fixer. Slides were stained with Hematoxylin and & Eosin. Examination and digital photomicrographs of the representative results were obtained using a digital camera mounted on an Olympus BX51 Microscope. The location of radioactivity is visualized on the slides as small black grains of silver precipitate generated from the emulsion exposed to the radioactive test article. Observations and conclusions are based on an evaluation of all samples. Conclusions regarding quantitative tissue concentrations cannot be made using MARG images.

G. Data Analysis

All response curves determined for image analysis calibration were generated using a weighted 1st degree, polynomial, linear equation (1/MDC/mm$^2$). A numerical estimate of goodness of fit was given by the relative error, where the absolute value for the relative error of each calibration standard was ≤0.250 to be accepted.

Standard Curve Calculations:

$$\text{Response } (MDC/\text{mm}^2) = a_1 \times \text{Concentration (Density-Standards in μCi/g)} + a_0$$

Where:

Density-Standards=concentration in μCi/g

MDC/mm$^2$=Molecular Dynamic Counts/area of tissue $a_1$=slope $a_0$=y-intercept The relative error for each standard was calculated using the standard curve according to:

$$\text{Relative Error} = \frac{\text{nominal concentration } (\mu Ci/g) - \text{calculated concentration } (\mu Ci/g)}{\text{nominal concentration } (\mu Ci/g)}$$

The LLOQ was determined as 3 times the mean background for each panel. Ten Target Regions were sampled to determine the mean for each panel.

LLOQ for healthy tissues=3×(0.00111)=0.0033 μCi/g
LLOQ for UC tissues=3×(0.00106)=0.0032 μCi/g Tissue concentration data were obtained using the profile image analysis sampling technique.

Profile imaging involved gathering concentration data at regular intervals (of 50 μm) across the image of each section using a ribbon-type sampling area provided by using the MCD "profile" function. Concentration data were obtained continuously through the section and correspond to the labeled layers of each sample.

III. RESULTS

A. Dose Formulation Analysis

The concentrations of radioactivity in the dose formulations averaged 4.53 and 48.7 nCi/mL (80.7 and 868 nM) for the pre-dose aliquots on the day of dosing. The coefficient of variations for analysis of triplicate aliquots of the formulations, each analyzed in triplicate, were 1.5 and 0.7%, respectively, which indicated that the formulations were homogeneous (Table, below).

| Tissue [a] | Group | Dose Level [b] | | | | % |
|---|---|---|---|---|---|---|
| | | Nominal | | Measured | | |
| | | nM | nCi/mL | nM | nCi/mL | CV |
| Healthy | 1 | 100 | 5.61 | 80.7 | 4.53 | 1.5 |
| | 3 | 1000 | 56.1 | 868 | 48.7 | 0.7 |
| Ulcerative Colitis | 2 | 100 | 5.61 | 80.7 | 4.53 | 1.5 |
| | 4 | 1000 | 56.1 | 868 | 48.7 | 0.7 |

[a] Total eight colon samples were used (two samples/group).
[b] Dose level was adjusted using the correction factor (1.264; total/free base).

The radiopurity of pre- and post-dose formulations was >96%.

B. Permeation Study

Permeation results of [$^{14}$C]Compound 1 in colon from healthy and UC subjects after 1 h incubation are listed in the Table below (where INCB039110 is Compound 1).

The inside of the tissue of subject 2 in group 2 was broken while attempting to cover one end of a polypropylene tube with the tissue securely, which might be due to loss in extensibility from UC condition. Although the permeation result of subject 2 in group 4 was not determined due to a leakage during 1 h incubation, this tissue sample was used for QARL and MARG. All [$^{14}$C]Compound 1 concentrations in basolateral side (receiver compartment) were below LLOQ.

C. Autoradiographic Analysis

QARL

Figure 3:
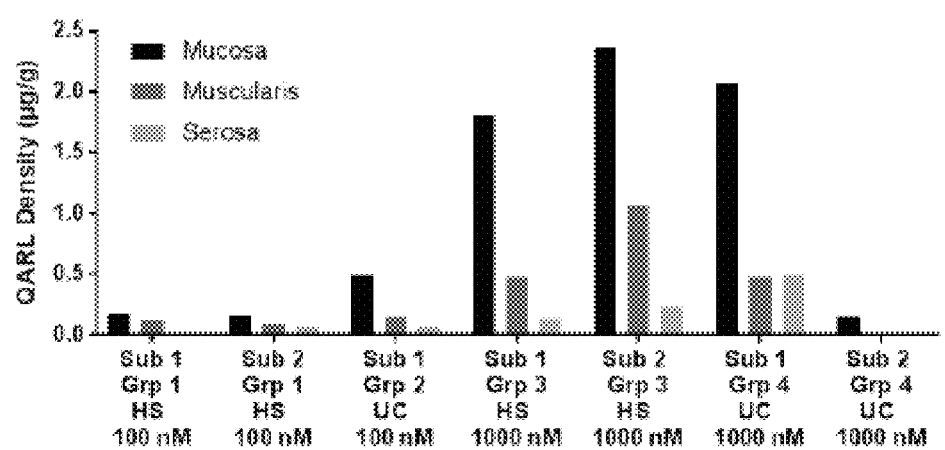
FIG. 3 depicts [$^{14}$C]Compound 1 concentrations in colon from healthy and ulcerative colitis subjects after 1 hour incubation.

A summary of the individual sample concentration profile data through sample layers is plotted in FIG. 3 and listed in the table below (where INCB039110 is Compound 1).

| | | | | [$^{14}$C]INCB039110 |
|---|---|---|---|---|
| | | | Colon | Concentration |
| Tissue | Group | Subject | Section | µCi/g |
| Healthy [a] | 1 | 1 | Mucosa | 0.173 |
| | | | Muscularis | 0.113 |
| | | | Serosa | BQL |
| | | 2 | Mucosa | 0.155 |
| | | | Muscularis | 0.090 |
| | | | Serosa | 0.059 |

Permeation of [$^{14}$C]INCB039110 in Colon from Healthy and Ulcerative Colitis Subjects after 1 h Incubation

| Time | Group | Subject | Sample | dpm in Sample Aliquot [d, e, f] | [$^{14}$C]INCB039110 Concentration [f] | | % of Dose Formulation |
|---|---|---|---|---|---|---|---|
| | | | | | nM | nCi/mL | |
| Healthy [a] | 1 | 1 | A | 462 | 74.2 | 4.16 | 91.8 |
| | | | B | 0 | 0 | 0 | |
| | | 2 | A | 473 | 75.9 | 4.26 | 94.0 |
| | | | B | 0 | 0 | 0 | |
| | 3 | 1 | A | 5029 | 807 | 45.3 | 93.1 |
| | | | B | 0 | 0 | 0 | |
| | | 2 | A | 4909 | 788 | 44.2 | 90.8 |
| | | | B | 0 | 0 | 0 | |
| UC [b, c] | 2 | 1 | A | 388 | 62.4 | 3.50 | 77.3 |
| | | | B | 0 | 0 | 0 | |
| | 4 | 1 | A | 4346 | 699 | 39.2 | 80.5 |
| | | | B | 0 | 0 | 0 | |

A: Apical side (mucosa, donor compartment, KRB buffer with test article); B: Basolateral side (serosa, receiver compartment: blank KRB buffer); UC: Ulcerative colitis

[a] A vertical Ussing diffusion chamber system was used for incubation.

[b] A Polypropylene tube with both end cut open was used for incubation.

[c] Subject 2 in group 2 was broken while covered the tube securely, which might be due to lose an extensibility from UC condition. A leakage was found in subject 2 in group 4 after 1 h incubation.

[d] Sample volume was 0.05 mL.

[e] All data presented have been substracted the background value (21 dpm)

[f] All data presented are mean value of duplicate.

-continued

[$^{14}$C]INCB039110 Concentrations in Colon from Healthy and Ulcerative Colitis Subjects after 1 h Incubation

| Tissue | Group | Subject | Colon Section | [$^{14}$C]INCB039110 Concentration µCi/g |
|---|---|---|---|---|
| | 3 | 1 | Mucosa | 1.802 |
| | | | Muscularis | 0.471 |
| | | | Serosa | 0.122 |
| | | 2 | Mucosa | 2.359 |
| | | | Muscularis | 1.062 |
| | | | Serosa | 0.226 |
| UC [b] | 2 | 1 | Mucosa | 0.491 |
| | | | Muscularis | 0.143 |
| | | | Serosa | 0.062 |
| | 4 | 1 | Mucosa | 2.059 |
| | | | Muscularis | 0.471 |
| | | | Serosa | 0.488 |
| | | 2 | Mucosa | 0.148 |
| | | | Muscularis | BQL |
| | | | Serosa | BQL |

BQL: Below quantification limit (<0.0033 µCi/g for healthy tissue and <0.0032 µCi/g for UC tissues);
UC: Ulcerative colitis
[a] A vertical Ussing diffusion chamber system was used for incubation.
[b] A Polypropylene tube with both end cut open was used for incubation.

The peaks collected represented variability in colon tissue layers. [$^{14}$C]Compound 1 was mainly distributed in mucosal layer but detected through submucosa layer (5 of 7 tissues).

MARG

No MARG reaction was observed in the first sets of slides (72 hours samples), subsequent slides developed a reaction that plateaued between 4-8 weeks. The relative concentrations of drug-derived radioactivity were consistent across tissue layers between samples, drug concentrations, and healthy and UC conditions. The highest concentrations were present in the villi and associated crypts across all samples, followed by the submucosa layer. Little to no radioactivity was observed in the muscular layer. Outside the muscular layer was at background.

Example 3: IL-6 Mediated STAT3 Phosphorylation and JAK1

Interleukin-6 (IL-6) signals through the common gp130 receptor and the specific IL-6Rα co-receptor to activate the Janus kinase (JAK)-signal transducer and activator of transcription (STAT) signaling pathway (Heinrich et al. *The Biochemical journal*. 2003; 374:1-20). Ulcerative colitis biopsies have identified IL-6 as the predominant cytokine within inflamed areas of the gut and its concentration is correlated with the Mayo endoscopic score (ref: Bernado et al., 2012). Aberrant inflammatory IL-6/STAT3 pathway activation has been described in peripheral blood mononuclear cell (PBMC) from rheumatoid arthritis patients (RA) (Isomäki, P et al. *Rheumatology*, Volume 54, Issue 6, 1 Jun. 2015, 1103-1113) and anti-IL-6 therapy demonstrates significant clinical efficacy (Expert Rev Clin Immunol. 2017 Jun.;13(6):535-551; *J Dermatolog Treat*. 2018 September; 29(6):569-578). The pathogenesis of plaque psoriasis (Ps) is driven by IL-23 mediated Thelper 17 (Th17)/IL-17 inflammation (refs). IL-6 plays a critical role in promoting STAT3-dependent induction of the IL-23 receptor, which in turn, is essential to confer full effector functions to Th17 cells (Zhou et al. *Nat. Immunol*. 2007; 8:967-974; Hirota et al. *J. Exp. Med*. 2007; 204:41-47; Calautti et al. *Int J Mol Sci*. 2018 January; 19(1): 171). Inhibition of signal transduction through the JAK/STAT pathway may be measured indirectly, in cytokine-driven cell based assays. Assessment of phosphorylated STAT levels are measured in response to stimulation of JAK1, often with recombinant human IL-6.

Figure 4:
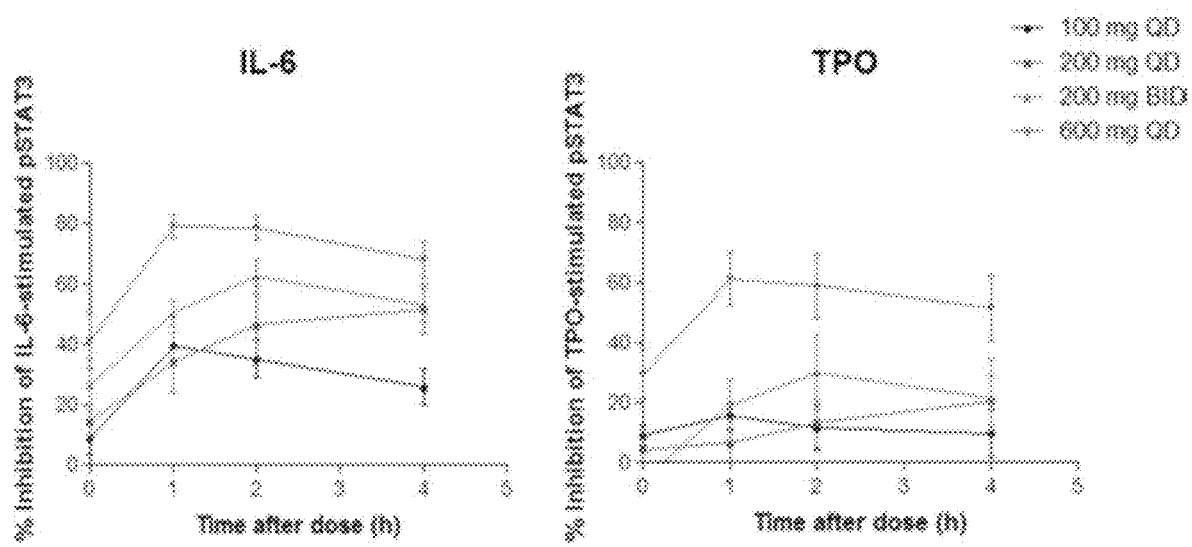
FIG. 4 depicts the change in IL-6 and TPO-induced STAT3 Phosphorylation by Compound 1 treatment group (PD Evaluable Subjects) in patients as described in Example 3.

The systemic effects of Compound 1 have been studied in the auto-immune diseases RA and Ps. Inhibition of phosphorylation of STAT3 following stimulation with IL-6, a marker of AK1 inhibition, and TPO, a marker of JAK2 inhibition was measured in both studies. In patients with Ps doses of 100 mg QD, 200 mg QD, 200 mg BID, and 600 mg QD were studied. There was a Compound 1-concentration dependent inhibition of pSTAT3 in response to IL-6 stimulation ex vivo. In response to TPO, however, there was no significant inhibition of pSTAT3 at doses of 100 mg QD, 200 mg QD, and 200 mg BID (FIG. 4). There was also a dose-dependent response in the primary efficacy measure mean change from baseline sPGA at Day 28 (see table below).

TABLE

Change from Baseline in Static Physician's Global Assessment at Day 28 in Patients with Plaque Psoriasis (Observed Cases in the mITT Population) (where INCB039110 is Compound 1)

| | | INCB039110 | | | |
|---|---|---|---|---|---|
| Variable | Placebo (n = 12) | 100 mg QD (n = 9) | 200 mg QD (n = 9) | 200 mg BID (n = 9) | 600 mg QD (n = 11) |
| Baseline sPGA score[a] | | | | | |
| n | 12 | 9 | 9 | 9 | 11 |
| Mean (SD) | 3.4 (0.51) | 3.2 (0.44) | 3.3 (0.71) | 3.1 (0.33) | 3.1 (0.30) |
| Median | 3.0 | 3.0 | 3.0 | 3.0 | 3.0 |
| Day 28 sPGA score | | | | | |
| n | 12 | 9 | 9 | 9 | 11 |
| Mean (SD) | 3.0 (7.4) | 2.6 (1.01) | 2.3 (1.00) | 2.0 (1.00) | 1.8 (0.98) |
| Median | 3.0 | 2.0 | 2.0 | 2.0 | 2.0 |

TABLE-continued

Change from Baseline in Static Physician's Global Assessment at Day 28 in Patients with Plaque Psoriasis (Observed Cases in the mITT Population) (where INCB039110 is Compound 1)

| | | INCB039110 | | | |
|---|---|---|---|---|---|
| Variable | Placebo (n = 12) | 100 mg QD (n = 9) | 200 mg QD (n = 9) | 200 mg BID (n = 9) | 600 mg QD (n = 11) |
| Percent change from baseline in sPGA score at Day 28 based on observed assessment | | | | | |
| n | 12 | 9 | 9 | 9 | 11 |
| Mean (SD) | −12.5 (15.69) | −22.2 (23.57) | −29.4 (31.14) | −35.2 (33.79) | −42.4 (26.21) |
| Median | 0 | −33.3 | −33.3 | −33.3 | −33.3 |
| p-value[b] | | 0.270 | 0.118 | 0.053 | 0.003 |

[a] Baseline was considered the last nonmissing sPGA measurement assessed before the first dose of study drug.
[b] Based on 2 sample t-tests between each active treatment group and placebo; no adjustment was made for multiple comparisons.

Figure 5:
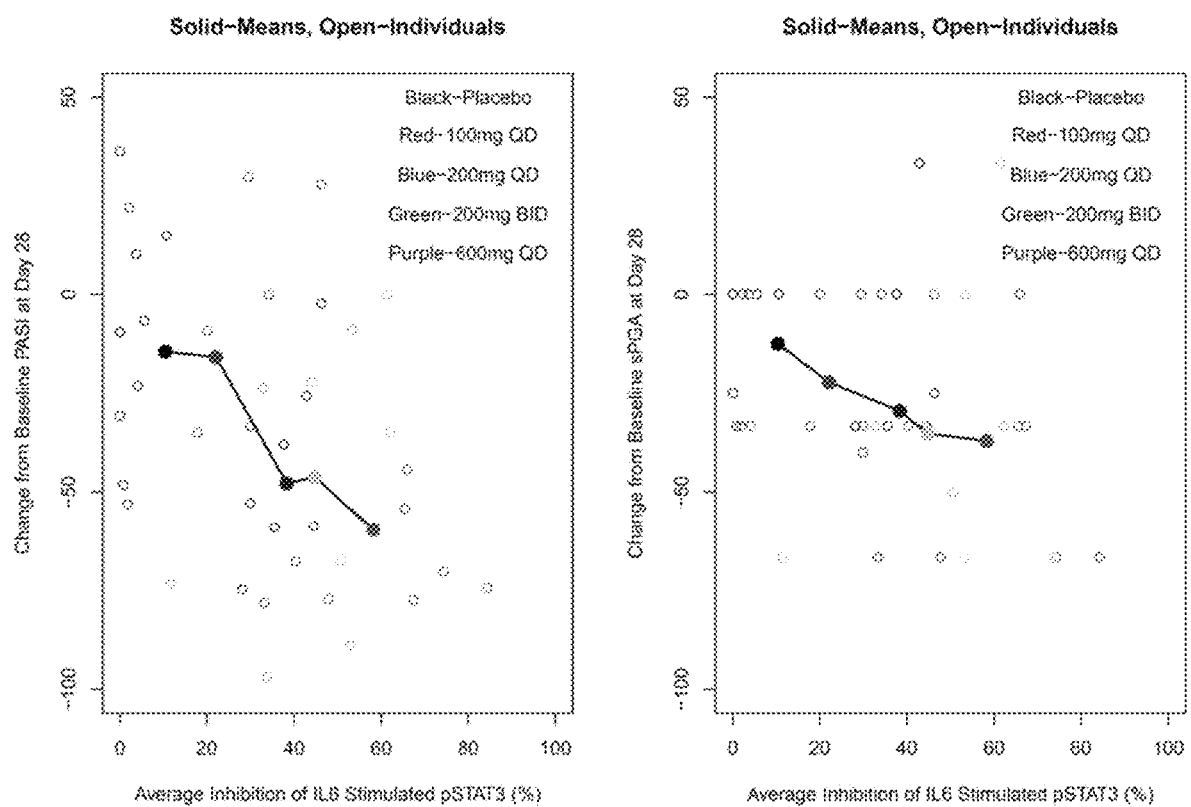
FIG. 5 depicts the correlation between IL-6 stimulated inhibition of phosphorylation of STAT3 and measures of efficacy (static physician's global assessment (sPGA) and psoriasis area and severity index (PAST) change from baseline) in patients as described in Example 3.

Doses of 200 mg BID (p=0.053) and 600 mg QD (p=0.003) demonstrated clinically meaningful changes from baseline while doses of 100 mg or 200 mg QD did not and were not statistically different than placebo (p=0.270, p=0.118, respectively). There is a good correlation between the pharmacodynamic marker of inhibition of ex vivo IL-6 stimulated STAT3 and efficacy endpoints (FIG. 5). No neutropenia was noted which is aligned with the observation that no significant inhibition of JAK2 (as determined from TPO stimulated pSTAT3 inhibition) was noted at doses of 100 mg QD, 200 mg QD, and 200 mg BID; neutropenia and other cytopenias are thought to be a result specifically of JAK2 inhibition precipitating myelosuppression (Bissonnette R et al *J Dermatolog Treat*, 2016 27(4)332-338, Mascarenhas et al. *Haematolgica* 2017 102(2):327-335).

Figure 6A:
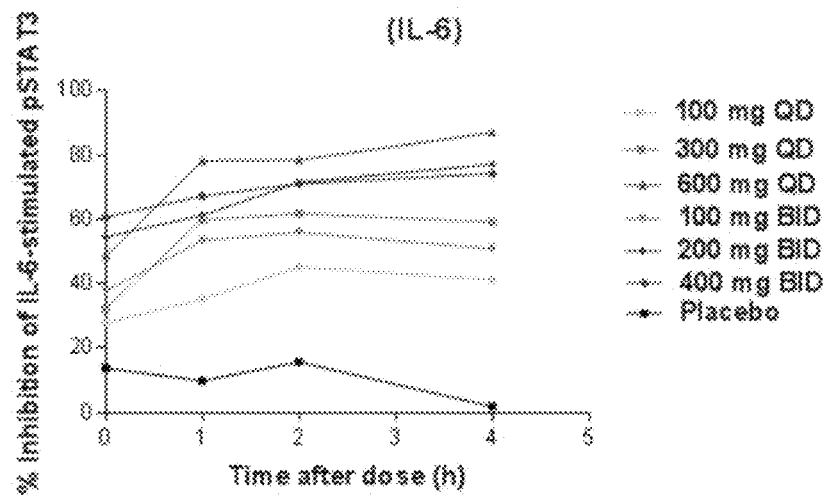
FIG. 6A depicts change in IL-6-Induced STAT3 Phosphorylation on Cycle 1 Day 15 in individuals as described in Example 3.
Figure 6B:
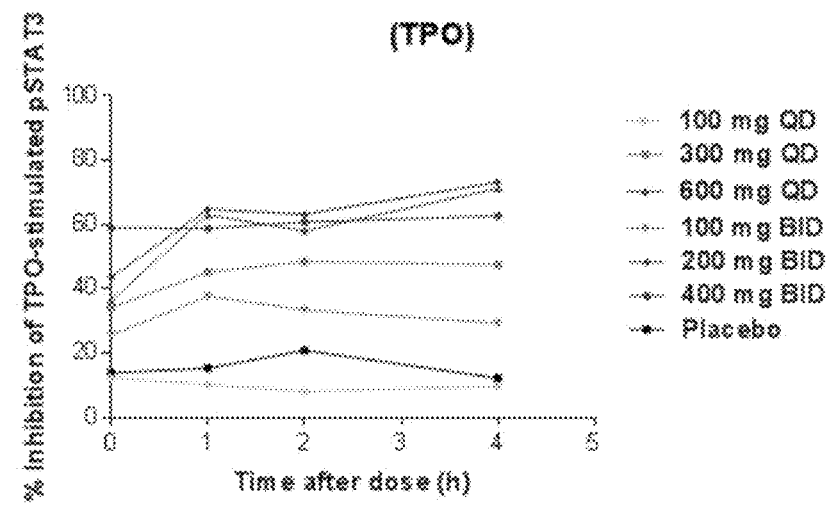
FIG. 6B depicts change in TPO-Induced STAT3 Phosphorylation on Cycle 1 Day 15 in individuals as described in Example 3.

In RA patients, doses of 100 mg QD and BID, 200 mg BID, 300 mg QD, 400 mg BID, and 600 mg QD were studied and again a general trend of dose-dependent inhibition of IL-6 induced pSTAT3 was observed (FIGS. 6A and 6B). A general trend of increasing TPO induced pSTAT3 inhibition was also observed. However, the greatest inhibition appeared to be observed following 200 mg BID dosing. Also noteworthy is that the 100 mg QD dose had less TPO induced pSTAT3 inhibition than placebo. In this study, there were several cases of decreased ANC but no dose-dependent trend was observed. With regard to efficacy, a dose dependent trend was not apparent across the dose range but statistically significant differences in ACR20, ACR50, and ACR70 responses were shown between Compound 1 and placebo for the 600 mg QD treatment group at the Day 84 visit (the primary endpoint visit).

Taken in totality, clinical data from RA and Ps patients suggest a 100 mg QD dose has minimal systemic effects based on aggregate safety, efficacy, and biomarker data. The daily exposure following 50 mg BID is expected to be lower than 100 mg QD given that Compound 1 displays supralinear PK with regard to dose.

Example 4: A Phase 2, Double-Blind, Dose-Ranging, Placebo-Controlled Study with Open-Label Extension to Evaluate the Safety and Efficacy of Compound 1 in Moderate to Severe Ulcerative Colitis I. Objective This study will evaluate the safety and efficacy of oral Compound 1 in participants with moderately to severely active UC. Compound 1 will be administered in an SR formulation. The oral bioavailability of Compound 1 in humans is moderate, with ~30% of the administered dose excreted intact as parent compound in the feces. Suppression of IL-6 stimulated phosphorylation of STAT3 is a measure of JAK1 inhibition. A dose of 50 mg BID Compound 1 is expected to result in fecal concentrations (~200 nM) that are in excess of the in vitro $IC_{50}$ value for suppression of IL-6 stimulated phosphorylation of STAT3 in PBMCs (58 nM). However, the corresponding plasma concentrations associated with this dose are expected to be low with a $C_{max}$ value (51 nM) that is well below the ex vivo whole blood $IC_{50}$ value of 141 nM. As a result, the efficacy of Compound 1 is expected to be mediated through predominantly local, rather than systemic, JAK1 inhibition.

As a selective and locally acting JAK1 inhibitor, Compound 1 may possess the anti-inflammatory properties seen with other JAK inhibitors without an associated risk of anemia or neutropenia. Given the favorable safety profile of Compound 1 in the selected dose range, concurrent use of immunosuppressive UC therapies (AZA, 6-MP, and methotrexate) will be permitted.

II. Overall Design

Approximately 206 participants will be enrolled overall in Part A (n=30) and Part B (n=176) for 12 weeks. Part A and Part B are both randomized, double-blind, placebo-controlled, and parallel designs.

In Part A, 30 participants will be randomly assigned to receive 50 mg BID or placebo in a 2:1 allocation ratio. Part A participants will complete an overnight, in-clinic visit at Week 4. At this visit, a 24-hour stool sample for fecal drug concentration analysis and serial blood samples for PK analysis of plasma drug concentration will be obtained. In addition to undergoing endoscopy at baseline and at Week 12, Part A participants (only) will undergo endoscopy at Week 4. Part A is intended to establish proof of mechanism at 50 mg BID in a 2:1 ratio, while Part B is intended to evaluate the clinical efficacy of a range of doses between 25 and 100 mg total daily dose given either QD or BID. Dose regimens to be used in Part B will be selected following Part A. Participants who complete either Part A or Part B and all relevant study procedures, including endoscopy at Week 12, are eligible to enter the corresponding 40-week OLE period of the study.

In Part B, 176 participants will be randomized to 1 of 3 dose levels of Compound 1 tablets or placebo in a 1:1:1:1 ratio. In addition to placebo, doses to be included in Part B are 25 mg BID, 50 mg BID, and 100 mg QD. Dose regimens in Part B will be confirmed at the conclusion of Part A (within a total daily dose range between 25 and 100 mg administered QD or BID). Part B participants will undergo an endoscopy at baseline and at Week 12. In addition, a total of 24 Part B participants (6 from each treatment group) will complete an overnight, in-clinic visit at Week 4. At this visit, a 24-hour stool collection for fecal drug concentration and serial blood samples for PK analysis will be obtained.

Background stable therapy for UC in both Part A and Part B should not be changed during the screening and double-blind treatment period until Week 12 assessments are completed.

Participants who require initiation of a new therapy for UC during this period should undergo an endoscopy and be withdrawn from the study with appropriate standard of care treatment given at the discretion of the investigator. After the Week 12 endoscopy, the daily corticosteroid dose may be increased or decreased at the discretion of the investigator. In addition to analyses of Week 12 data from Part A and Part B, there are 3 additional interim analyses also planned for this study:

1. The first interim analysis will be performed when 15 participants randomized in Part A have Week 4 data available. The unblinded PK/PD team will evaluate systemic exposure and perform preliminary biomarker analyses to ascertain whether Compound 1 has an effect on JAK/STAT signaling pathways.

2. The second interim analysis will be performed when these 15 participants reach Week 12. In addition to considering PK/PD results, if there is insufficient evidence of efficacy demonstrated in this section, the study may be terminated.

3. The third interim analysis will be performed after 88 participants randomized in Part B have Week 12 data available. The study may be terminated if there is insufficient evidence of efficacy.

At the conclusion of Part A, the SRC (comprised of members of the sponsor's study team) will conduct a final analysis for Part A to review all safety and PD data on an unblinded basis in order to decide whether to proceed to Part B or to terminate the study. Selection of dose regimens for Part B will be informed by this analysis of data. Part B dose regimens will be either QD or BID with a total daily dose between 25 and 100 mg. In addition, dose regimens in the Part A and Part B OLE periods may be modified by the sponsor's study team based on Part A results). The dose in the Part A OLE is 50 mg BID. Doses in the Part B OLE period may later be modified within the same dose range (25 mg to 100 mg total daily dose).

When 88 participants have completed Week 12 of Part B, the DMC may make recommendations to continue the study (no details about the results of the current safety analysis will be revealed before the next scheduled analysis) or may recommend stopping the study (based on lack of efficacy or any safety finding). They may also make recommendations regarding modification of the OLE doses for Part B.

The final analysis of the double-blind period will be conducted when all Part B participants have completed Week 12.

The final study analysis will occur after all participants have completed the OLE period of the study, including the 30-day follow-up period.

III. Study Treatment

| | |
|---|---|
| Study treatment name: | Compound 1 |
| Dosage formulation: | SR tablet |
| Unit dose strength(s)/ dosage level(s): | 25 mg (white tablet) and matching placebo. In both Part A and Part B, participants randomized to QD regimen will receive blinded study treatment BID. |
| Route of administration: | Oral |
| Administration instructions: | For Part A and Part B at Weeks 2, 4, and 12, study drug will be administered at the site after the predose PK sample is drawn. For all other visits, the morning dose will be self-administered by the participant at home prior to the scheduled visit without regard to food. Note: The dosing schedule in Part B will be determined following Part A. In both Part A and Part B, participants randomized to QD regimen will receive blinded study treatment BID. Missed doses may be taken within 6 hours after the scheduled time of administration. |
| Packaging and labeling: | Study drug will be provided in bottles. Investigational product labels will be in the local language and will be labeled as required per country requirement. |
| Storage: | Ambient 15° C.-30° C. (59° F.-86° F.) |

IV. Efficacy Assessment

The definitions for efficacy endpoints based on Mayo score are defined below will be used throughout the Protocol.

A. List of Definitions for Efficacy Endpoints Based on Mayo Score

| Term | Definition |
| --- | --- |
| Clinical Remission | Stool frequency subscore of 0, rectal bleeding subscore of 0, modified Mayo Endoscopy Score (mMES) score of 0 or 1. |
| Clinical Response | A decrease from baseline in the 3-component Mayo score of at least 2 points and at least 30% decrease from baseline with an accompanying decrease in the subscore for rectal bleeding of at least 1 point or an absolute subscore for rectal bleeding of 0 or 1. |
| Endoscopic Remission | An mMES score of 0. |
| Endoscopic Response | A decrease from baseline in the mMES score by at least 1 point. |
| Mucosal Healing | An mMES score of 0 or 1. |

B. Endoscopy

Endoscopy examination (preferably colonoscopy) is required at baseline and Week 12. In addition, endoscopy (colonoscopy or flexible sigmoidoscopy at the sites' discretion) is required at Week 4 for all Part A participants only. This procedure will be performed in order to establish the 3-component Mayo score, including the mMES in which any friability results in a score of at least 2 (Food and Drug Administration. Guidance for Industry: Ulcerative Colitis: Clinical Trial Endpoints. 2016. https://www.fda.gov/downloads/Drugs/GuidanceCompli-anceRegulatoryInformation/Guidances/UCM515143.pdf). The duration of the time between endoscopies and the scheduled visits should not exceed 14 days. The endoscopy will also allow for pinch biopsy to evaluate PD effect in mucosal tissue.

A trained endoscopist should perform the endoscopy. Where possible, the same endoscopist should perform the endoscopy at all visits. All results will be centrally read and adjudicated as described in the Study Manual.

Histological assessments of biopsy specimens obtained during endoscopy may also be reviewed by trained pathologists as described in a separate charter.

C. Inflammatory Bowel Disease Questionnaire (IBDQ)

The IBDQ is a psychometrically validated patient-reported outcome instrument for measuring the disease-specific quality of life in participants with inflammatory bowel disease, including UC. The IBDQ comprises 32 items, which are grouped into 4 dimensions that are scored as follows:

Bowel symptoms: 10 to 70.
Systemic symptoms: 5 to 35.
Emotional function: 12 to 84.
Social function: 5 to 35.

The total IBDQ score ranges from 32 to 224. For the total score and each domain, a higher score indicates better quality of life. A score of at least 170 corresponds to Clinical Remission and an increase of at least 16 points is considered to indicate a clinically meaningful improvement.

The IBDQ will be assessed at baseline and at each specified study visit.

D. 3-Component Mayo Score

The 3-component Mayo score will be used to measure disease activity of UC in this study. The 3-component Mayo score (Mayo score without PGA, ranges from 0 to 9 points), consists of the following 3 subscores, each graded from 0 to 3 with higher scores indicating more severe disease:

Stool frequency (0-3)
Rectal bleeding (0-3)
mMES (0-3)

The 3-component Mayo score will be determined at baseline and at each specified study visit, based on incorporating endoscopy results as assessed by a central reader.

When a central endoscopic result is missing, endoscopic subscore as determined by the investigator will be used in the calculation.

The 3-component Mayo score is calculated using the stool frequency and rectal bleeding data from the most recent 3 days of available data prior to the visit. Data collected from the following periods will not be included in this calculation:

The day medications for constipation or diarrhea are taken.
The day of a procedure or preparation for a procedure (e.g., enemas, other laxative, clear liquid diet) affecting stool frequency or blood content.
The 48 hours following use of anti-motility agents (e.g., loperamide).
The 48 hours following endoscopy.

E. Physician's Global Assessment

The PGA will be calculated apart from the 3-component Mayo score. The PGA acknowledges the following 3 criteria:

The participant's daily recollection of abdominal discomfort, and
The participant's general sense of well-being, and
The participant's other observations, such as physical findings and the participant's performance status.

The PGA criteria will be scored as follows:
0=Normal
1=Mild disease
2=Moderate disease
3=Severe disease The PGA will be assessed at baseline and at each specified study visit.

V. Pharmacokinetic Assessments

A. Blood and Stool Sample Collection

At PK visits (Weeks 2 and 12), participants must refrain from taking study drug before arriving at the research site. A predose PK sample should be collected. Following collection of the predose PK sample, Compound 1 will be administered, and subsequent timed samples will be collected from participants. The date and time of blood collection for PK analysis; of the last dose of study drug; and of the last 2 meals preceding the blood draw (e.g., dinner the previous night and breakfast that morning) will be recorded.

At Week 4, all participants in Part A and a subset of Part B participants (n=~24) will complete an overnight, in-patient clinic visit. At this visit, participants will collect a 24-hour stool sample to determine Compound 1 fecal concentrations in the stool and serial blood samples for analysis of plasma drug concentrations will be obtained (See, e.g., Example C). An endoscopy (colonoscopy or flexible sigmoidoscopy) will be performed before the participant is discharged from the CRU and assessed by a central reader.

TABLE

Pharmacokinetic Blood Sample Timing

| Study Visit[a] | Timing of Sample Relative to Study Drug Administration | | | | | | |
|---|---|---|---|---|---|---|---|
| | Predose (−30 min) | 1 h ± 15 min | 2 h ± 30 min | 5 h ± 30 min | 8 h ± 60 min | 12 h ± 60 min | 24 h ± 60 min |
| Week 2 | X | X | X | — | — | — | — |
| Week 4 | X | X | X | X | X | X | X |
| Week 12 | X | X | X | — | — | — | — |

[a]All participants will have predose, 1-hour, and 2-hour samples sample collected at Weeks 2, 4, and 12. Only a subset of participants (i.e., those in Part A and approximately 24 from Part B) will have additional blood sampling at Week 4 (5, 8, 12, and 24-hour sampling) and stool collection for 24 hours at Week 4.

VI. Objectives and Endpoints

| Objectives | Endpoints |
|---|---|
| Primary | |
| To evaluate the efficacy of Compound 1 in inducing a Clinical Response in participants with moderate to severe UC. | Proportion of participants with a Clinical Response at Week 12. |
| Secondary | |
| To evaluate the efficacy of Compound 1 on endoscopic, clinical, and Quality of Life outcomes in participants with moderate to severe UC. | Proportion of participants with Endoscopic Response at Week 12. Proportion of participants with Mucosal Healing at Week 12. Proportion of participants in Endoscopic Remission at Week 12. Proportion of participants in Clinical Remission at Week 12. Proportion of participants in each of the 3-component Mayo subscores. Change from baseline at Week 12 in 3-component Mayo score. Change from baseline to Week 12 in PGA score. Change in Quality of Life score as measured by the IBDQ at Weeks 4 and 12. |
| To explore the safety and tolerability of Compound 1 in participants with UC. | Monitoring the incidence, duration, and severity of AEs; performing physical examinations; collecting vital signs; and collecting ECGs and laboratory data for hematology, serum chemistry, and urinalysis. |
| To explore the PK of Compound 1 in participants with UC. | Plasma concentrations of Compound 1 at Weeks 2, 4, and 12 for determination of $C_{min}$, $C_{max}$ and, data permitting, $AUC_{0-\tau}$, CL/F, $V_z$/F, half-life, and $T_{max}$. Stool concentrations of Compound 1 at Week 4 following 24-hour collection. |

Example 5. Pre-Clinical Mouse Model of Spontaneous Colitis

The interleukin-10 (IL-10) knockout (KO) mouse model mirrors the multifactorial nature of inflammatory bowel disease (IBD), such as ulcerative colitis and Crohn's disease, as IL-10 KO mice, BALB/cAnNTac-1110$^{em7Tac}$, spontaneously develop colitis. Colitis in IL-10 KO mice results from an aberrant response of CD4$^+$ T helper 1-like T cells and an excessive secretion of the proinflammatory cytokines that signal through the Janus kinase/signal transducers and activators of transcription (JAK/STAT) pathway. Compound 1 is a potent JAK1 inhibitor with 22 to >500-fold selectivity for JAK2, JAK3 and TYK2, and is currently being investigated as a monotherapy in a clinical trial for moderate-to-severe ulcerative colitis.

Female IL-10 homozygote knockout mice on the BALB/c strain background were provided by Taconic (USA). From 6 weeks of age onwards, Compound 1 and vehicle (10 mL/kg) were administered by oral gavage twice daily. Diarrhea was quantified on a 0-3 rating scale, (0=normal; 1=soft but still formed; 2=very soft; 3=diarrhea). Mice were euthanized by $CO_2$ asphyxiation and colon length and weight measured. Tissue pathology was scored on a scale of 0 to 10 based on the following criteria: Lymphocytic infiltrate in the mucosa and the gut associated lymphoid tissue located in the lamina propria/submucosa, mucosal erosions/ulcerations, and transmural inflammation. Body weight, stool consistency, fecal occult blood and rectal bleeding were scored. The incidence of rectal prolapse was recorded.

Figure 7A:
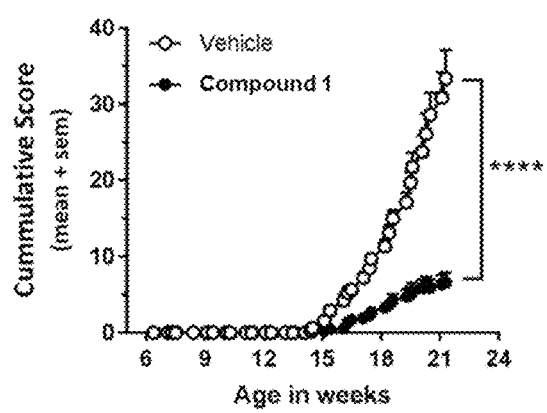
FIGS. 7A-7D show twice daily Compound 1 treatment (30 mg/kg) reduces symptoms (FIG. 7A), gross tissue abnormality (FIG. 7B), and histological evidence of tissue pathology (FIGS. 7C-7D) in the IL-10 knockout mouse model of spontaneous colitis. Data represents mean+sem, n=9-10 per treatment group. *$p<0.05$, *$p<0.001$, **$p<0.0001$.
Figure 7B:
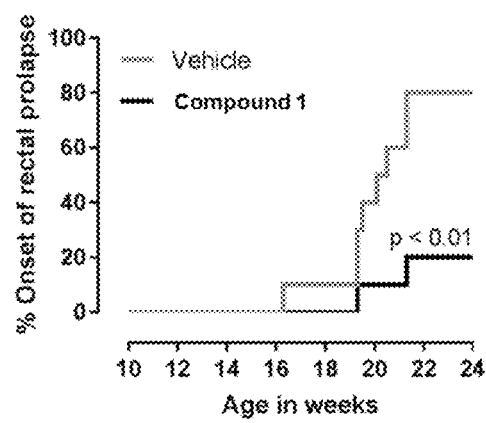
Figure 7C:
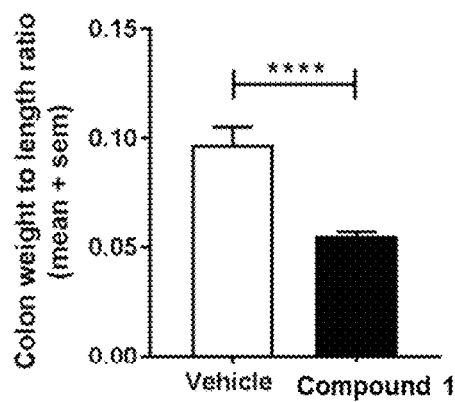
Figure 7D:
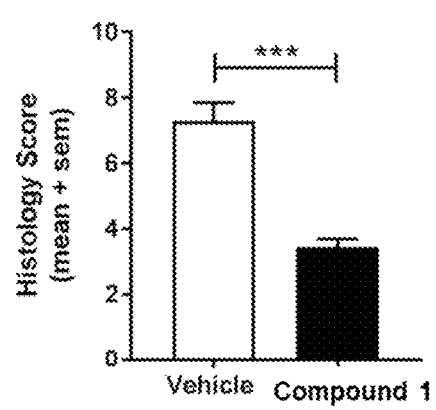
Figure 10:
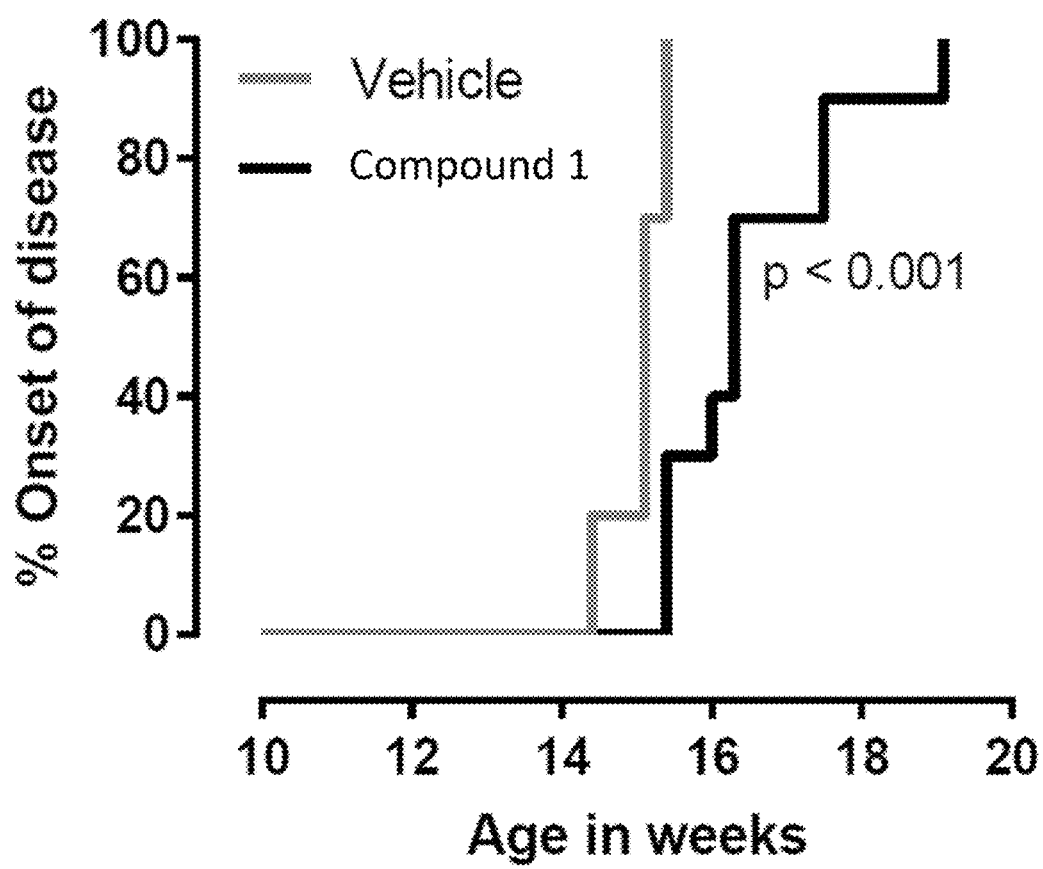
FIG. 10 shows results of twice-daily treatment with Compound 1 at 30 mg/kg inhibited disease onset in the IL-10 knockout (KO) mouse model of spontaneous colitis. Data represents mean+SEM, n=9-10 per treatment group, and p values were calculated using Kaplan-Meier survival curve analysis. SEM, standard error of the mean.
Figures 15A, 15B:
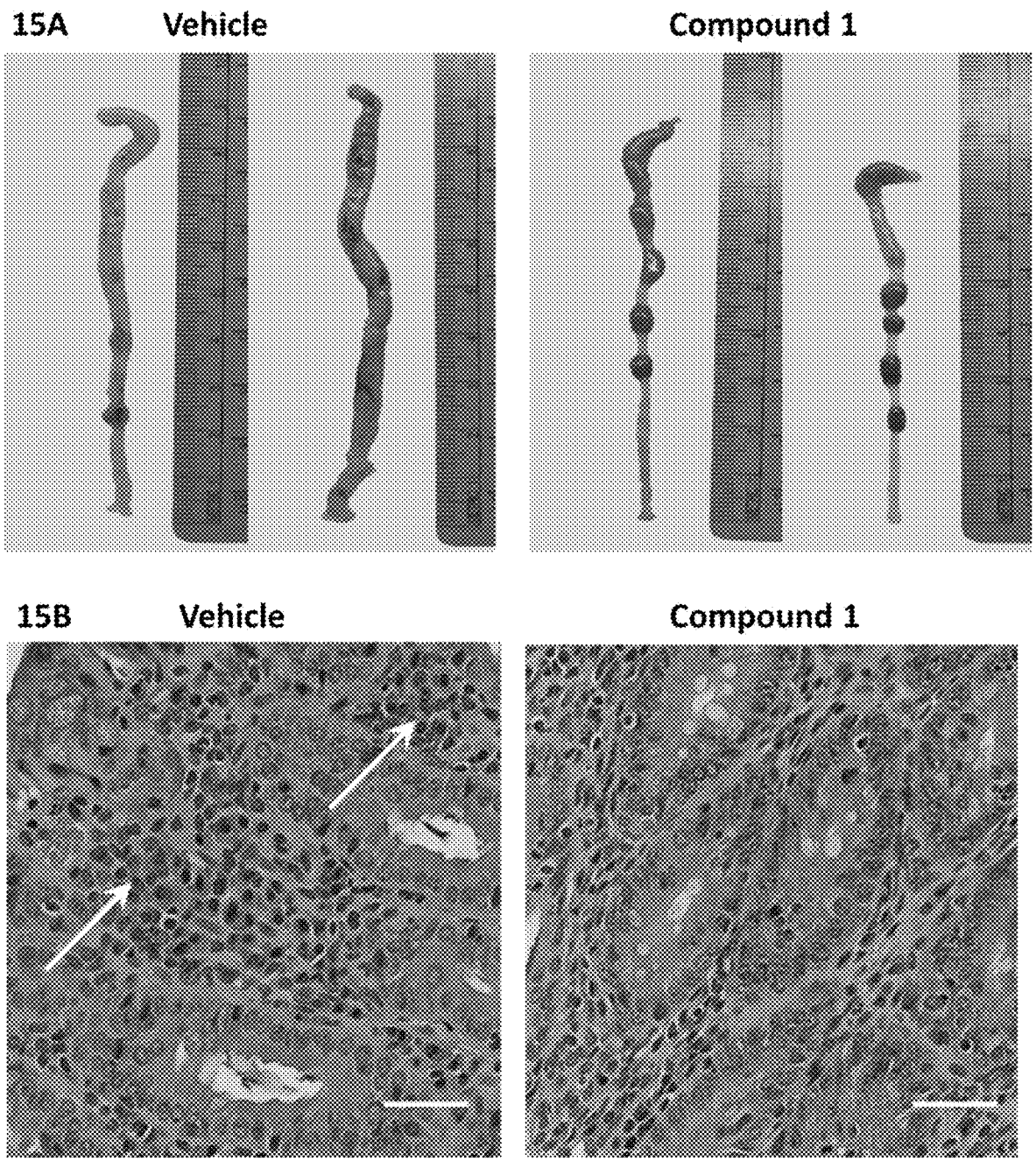
FIGS. 15A-15B show that systemic Compound 1 delivery is associated with significant protective effects on colon morphology in IL-10 KO mouse.

Significant improvements were observed on total disease burden, as shown in FIG. 7A, and the onset of rectal prolapse as a marker of severe disease, as shown in FIG. 7B. Ex vivo, the colon tissue of Compound 1 treated mice were characterized by reduced tissue pathology, as shown in FIGS. 7C-7D. Oral twice daily administration of Compound 1 at 30 mg/kg significantly (p<0.001) delayed colitis onset and modulated disease-associated weight loss. Cumulative clinical disease score was significantly (p<0.0001) reduced in the animals treated with Compound 1 compared to vehicle control. Incidence of rectal prolapse was also significantly (p<0.01) lower. Administration of Compound 1 resulted in significant (p<0.01) reduction in colon structural pathology. Lymphocytic infiltration and transmural inflammation were also significantly (p<0.01) decreased in the mice treated with Compound 1 versus vehicle control. As shown in FIG. 10, it was also found that Compound 1 ameliorated spontaneous colitis in the IL-10 KO mouse model, as evidenced by significantly slower disease onset, and that Compound 1 treatment resulted in differential gene expression profiles in the colon of IL-10 KO mice as compared to vehicle control, as shown in FIGS. 12A-12B. As shown in FIGS. 15A-15B, systemic Compound 1 delivery was associated with significant protective effects on colon morphology in IL-10 KO mouse.

These data suggest that Compound 1 may be useful as a therapeutic agent for the treatment of IBD (e.g. spontaneous colitis).

Example 6

Experimentally Induced Inflammatory Bowel Disease in Mouse Model

Inflammatory bowel disease (IBD), such as ulcerative colitis and Crohn's disease, is a group of idiopathic chronic and relapsing inflammatory conditions resulting from a complex interaction between the immune system and tissues of the gastrointestinal tract. Multiple cytokines and growth factors in the pathogenesis of IBD signal through the Janus kinase/signal transducers and activators of transcription pathway.

Preclinical models of IBD were established in BALB/c mice by intracolonic injection of 2,4,6-trinitrobenzene sulfonic acid (TNBS) or 4-ethoxymethylene-2-phenyl-2-oxazolin-5-one (oxazolone) to trigger an immune response, as described below. Body weight, stool consistency and fecal blood were scored. Additional readouts included colon weight to length ratio and histological evaluation. Blood was collected for pharmacokinetic analysis.

Mouse Oxazolone Induced Colitis Model

Male BALB/c mice were commercially purchased (Charles River Laboratories). On day 0, mice were sensitized by applying oxazolone (150 μL, 3% in acetone/olive oil, 4:1 v/v) to their preshaved rostral back. The animals were re-sensitized with oxazolone on Day 5. Mice were fasted before intra-rectal oxazolone challenge. Distal colitis was induced by intracolonic instillation of oxazolone solution (1 mg in 0.1 mL 40% ethanol) after which, animals were kept in a vertical position for 30 seconds to ensure that the solution remained in the colon. Sham control mice received 0.1 mL 40% ethanol alone. Compound 1 and vehicle (10 mL/kg) were administered by oral gavage twice daily. Diarrhea was quantified on a 0-3 rating scale, (0=normal; 1=soft but still formed; 2=very soft; 3=diarrhea). Fecal occult blood was detected on a 0-3 scale using S-Y occult blood paper (Shih-Yung Medical Instruments, Taiwan), (0=negative; 1=positive; 2=visible blood traces; 3=rectal bleeding). On Day 8, the mice were euthanized by $CO_2$ asphyxiation and colon length and weight measured. Furthermore, when the abdominal cavity was opened adhesions between the colon and other organs were noted as was the presence of colonic ulceration after removal and weighing of each colon. Macroscopic scoring was performed on a 0-12 scale, as shown in Table A. Normalized colon weight represents the increase in tissue relative to sham control mice.

TABLE A

| Parameter | Observation | Score |
|---|---|---|
| Adhesions | None | 0 |
| | Minimal | 1 |
| | Involving several bowel loops | 2 |
| Strictures | None | 0 |
| | Mild | 2 |
| | Severe, proximal dilatation | 3 |

TABLE A-continued

| Parameter | Observation | Score |
|---|---|---|
| Ulcers/ | No damage | 0 |
| Inflammation | Focal hyperemia, no ulcers | 1 |
| | 1 site of ulceration/inflammation <1 cm | 2 |
| | 2 sites of ulceration/inflammation <1 cm | 3 |
| | Major site(s) of ulceration/inflammation >1 cm | 4 |
| | If damage >2 cm increase score by 1 for each additional cm of damage | 5+ |
| Wall thickness | <1 mm | 0 |
| | 1-3 mm | 1 |
| | More than 3 mm | 2 |

Intra-rectal administration of oxazolone in an ethanol vehicle triggers direct tissue damage and inducing an immune response that leads to mucosal inflammation, epithelial micro-ulcerations and histopathological changes in the distal colon are reminiscent of human ulcerative colitis (see e.g., Kojima et al, *J. Pharmacol. Sci.* 2004, 96(3):307-313). The latter inflammation phase is driven by the production of Th2 cytokines, such as IL-4, IL-5 and IL-13 secretion (see e.g., Randhawa et al, *J. Physiol. Pharmacol.* 2014, 18(4):279-288).

Figures 8A, 8B, 8C:
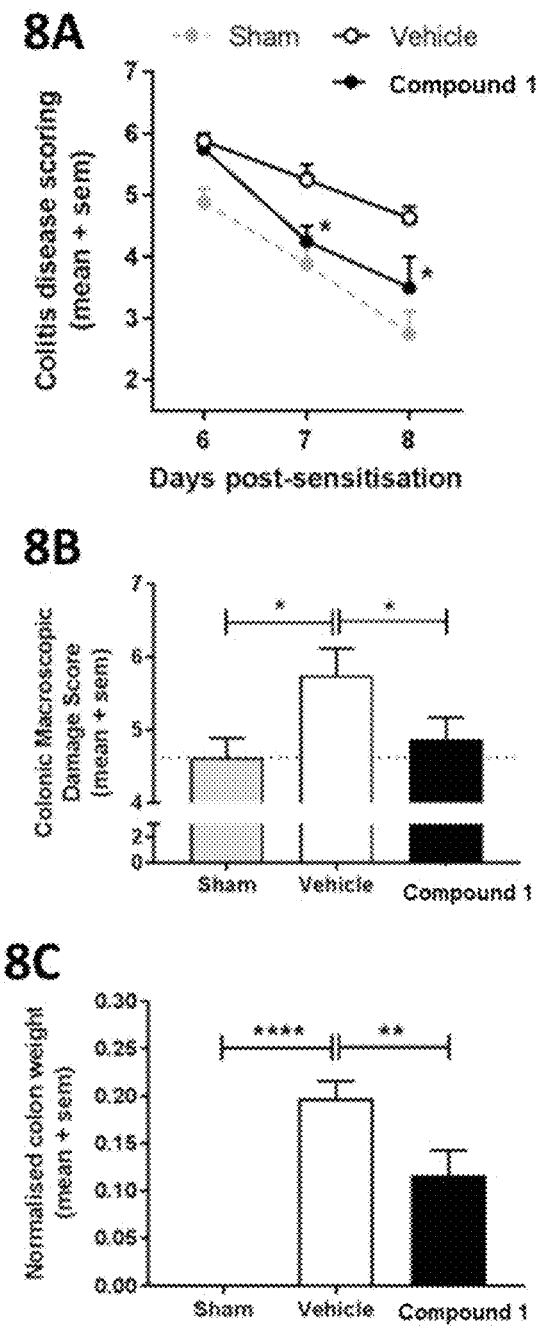
FIGS. 8A-8C show twice daily Compound 1 treatment (30 mg/kg) reduces symptoms (FIG. 8A), tissue damage (FIG. 8B), and inflammatory swelling (FIG. 8C) in the mouse model of oxazolone-induced colitis. Data represents mean+sem, n=8 per treatment group. Non-parametric two-tailed Kruskal-Wallis with Dunn's test for colitis disease and macroscopic assessments. Parametric two-tailed ANOVA with Holm-Sidak's test for colon weight analysis *$p<0.05$, $p<0.01$, **$p<0.0001$.

Daily Compound 1 treatment (30 mg/kg BID) was efficacious in accelerating recovery from diarrhea and rectal bleeding, as shown in FIG. 8A, ameliorating macroscopic tissue pathology, as shown in FIG. 8B, and reducing normalized colon weight as a surrogate readout for inflammatory swelling, as shown in FIG. 8C. These data are consistent with published results demonstrating that tofacitinib inhibits oxazolone-induced colitis (see e.g., Beattie et al, *J. Inflamm.* (Lond). 2017, 14:28) and suggest a significant proportion of the anti-inflammatory efficacy is driven by JAK1 inhibition. In addition, twice-daily Compound 1 treatment (orally or intracolonically significantly ameliorated stool consistency and reduced fecal occult blood scoring compared to vehicle-treated controls (see FIGS. 13A-13D), and Compound 1 treatment significantly ameliorated colon shortening as compared to respective vehicle-treated controls (see FIGS. 14A-14E).

TNBS-Induced Colitis Model

Male BALB/c mice were purchased (Charles River Laboratories) and distal colitis was induced by intracolonic instillation of TNBS (2,4,6-trinitrobenzenesulfonic acid solution, 1 mg in 0.1 mL 50% ethanol). Compound 1 treatment was administered at 30 mg/kg by oral gavage (PO) or 3 mg/kg by intracolonic injection (IC) twice daily (BID). Diarrhea was quantified on a 0-3 rating scale, (0=normal; 1=soft but still formed; 2=very soft; 3=diarrhea) on days 3 to 5 post TNBS sensitization.

Figure 9A:
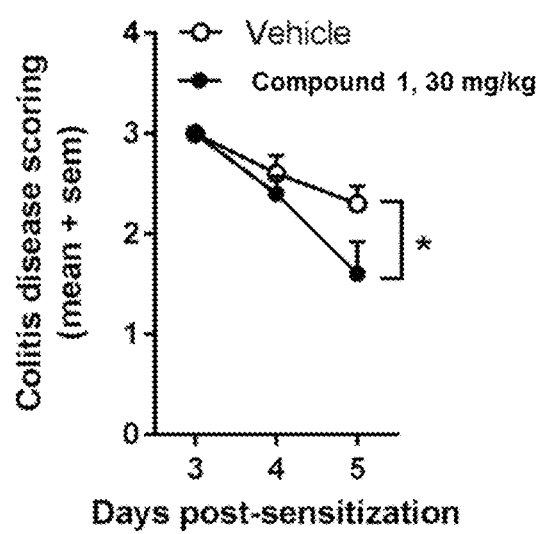
FIGS. 9A-9B show twice daily Compound 1 treatment administered orally (FIG. 9A) or via intracolonic injection (FIG. 9B) significantly reduced disease severity in the TNBS-induced colitis model in mice. Data represents mean+sem, n=3-8 per treatment group. *$p<0.05$, **$p<0.01$.
Figure 9B:
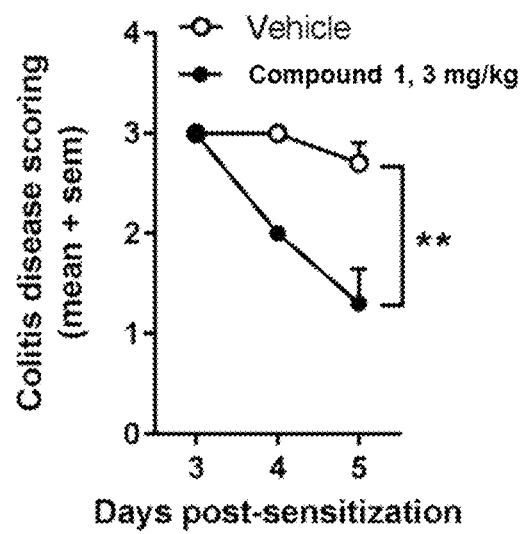

Oral Compound 1 treatment significant diarrhea symptoms compared to vehicle treated animals, as shown in FIG. 9A. This data is consistent with the oxazolone induced model data shown in FIG. 8A. Low dose Compound 1 treatment delivered directly to the colon was also highly efficacious in enhancing disease recovery, as shown in FIG. 9B. For example, in the oxazolone model, Compound 1 at 30 mg/kg PO BID showed significant (p<0.05) reduction in colon shortening (see FIGS. 14A-14B and 14E) and weight gain. Compound 1 at 3 mg/kg IC BID also significantly (p<0.05) reduced colon shortening (see FIG. 14C-14E).

Twice daily oral dose (PO) of Compound 1 at 30 mg/kg or 3 mg/kg intracolonical dose significantly (p<0.05) improved stool consistency compared to control. In addition, a significant (p<0.05) decrease in fecal blood score was achieved at 3 mg/kg IC BID. Moreover, both routes of administration (oral, IC) resulted in significant (p<0.05) improvement of stool consistency and fecal blood score. Compound 1 at 3 mg/kg IC BID ameliorated total colonic macroscopic damage. Intracolonic doses of Compound 1 maintained systemic drug exposure below JAK1 $IC_{50}$, but achieved comparable inhibition of experimental IBD. Together, these data suggest that Compound 1 may be useful as a therapeutic agent for the treatment of IBD.

Figure 11A:
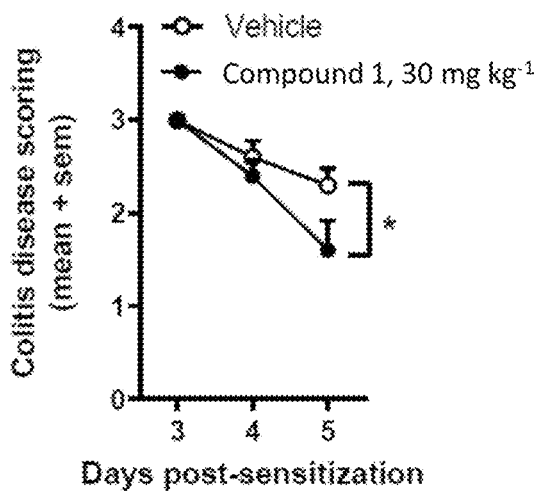
FIGS. 11A-11D show that twice-daily treatment with Compound 1 either orally (FIG. 11A) or via intracolonic injection (FIG. 11B) significantly reduced disease severity in the TNBS-induced colitis model in mice. High-dose oral (FIG. 11C) and low-dose intracolonic (FIG. 11D) achieved sustained drug exposures above $IC_{50}$ coverage. Data represent mean+SEM, n=8 per treatment group. IBD, inflammatory bowel disease; SEM, standard error of the mean. *p<0.05, **p<0.01.
Figure 11B:
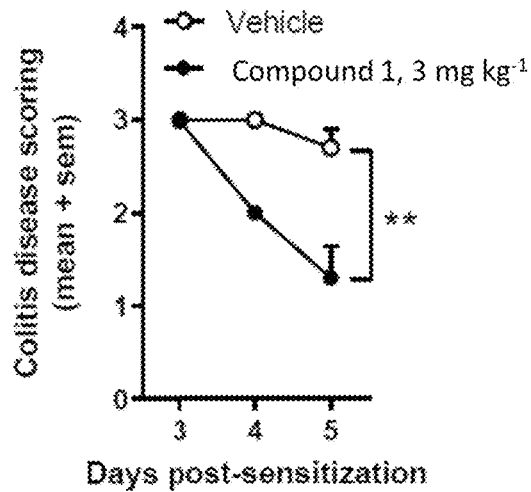

Intrarectal administration of the haptenating agent (TNBS) renders colonic proteins immunogenic to the host immune system and thereby initiates a T helper (Th)1-mediated immune response characterized by infiltration of the lamina propria with CD4+ T cells, neutrophils, and macrophages. Compound 1 was administered orally at 30 mg/kg or directly into the colon at 3 mg/kg to determine if localized JAK1 inhibition would be efficacious. Consistent with the oxazolone model, oral Compound 1 accelerated disease score recovery compared to vehicle treated animals, as shown in FIG. 11A. Low dose Compound 1 administered directly into the colon more rapidly induced recovery and appeared to mediate a greater therapeutic response, as shown in FIG. 11B.

Figure 11C:
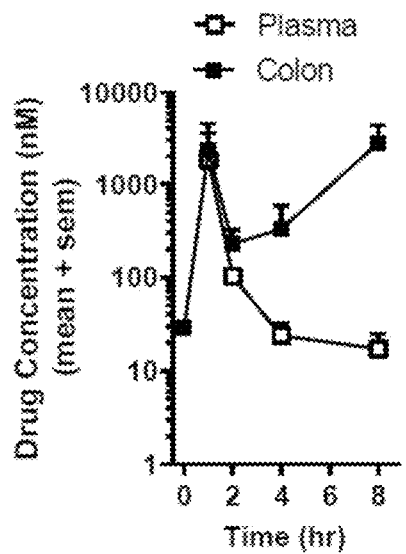
Figure 11D:
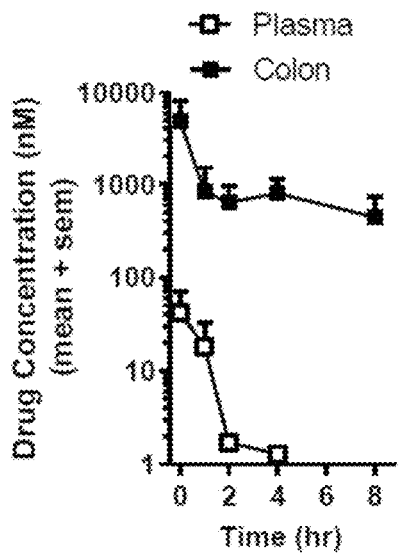
Figure 13A:
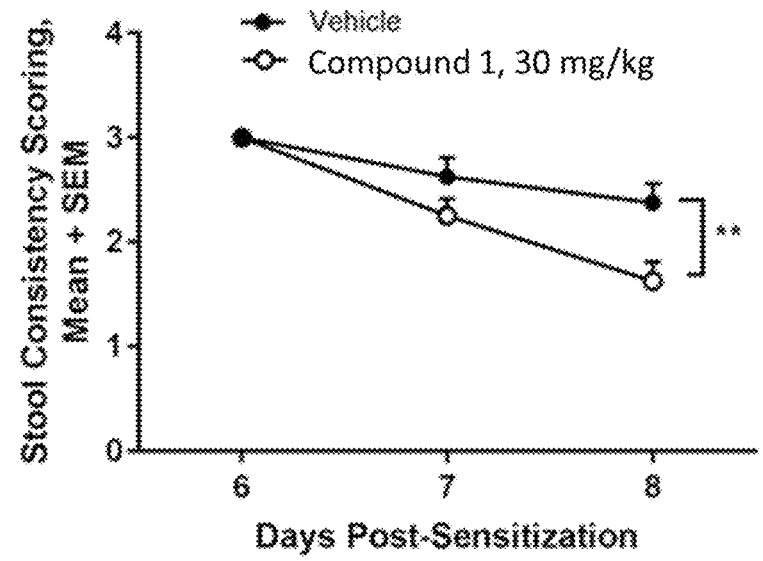
FIGS. 13A-13D show results of systemic and localized intracolonic Compound 1 delivery in the oxazolone-induced murine model of inflammatory bowel disease (IBD). Twice-daily Compound 1 treatment was administered orally (FIGS. 13A, 13C) or intracolonically (FIGS. 13B, 13D) significantly ameliorated stool consistency and reduced fecal occult blood scoring in the oxazolone-induced colitis model in mice. Data represent mean+SEM, n=8 per treatment group. SEM: standard error of the mean. p<0.01, *p<0.001, ****p<0.0001.
Figure 13B:
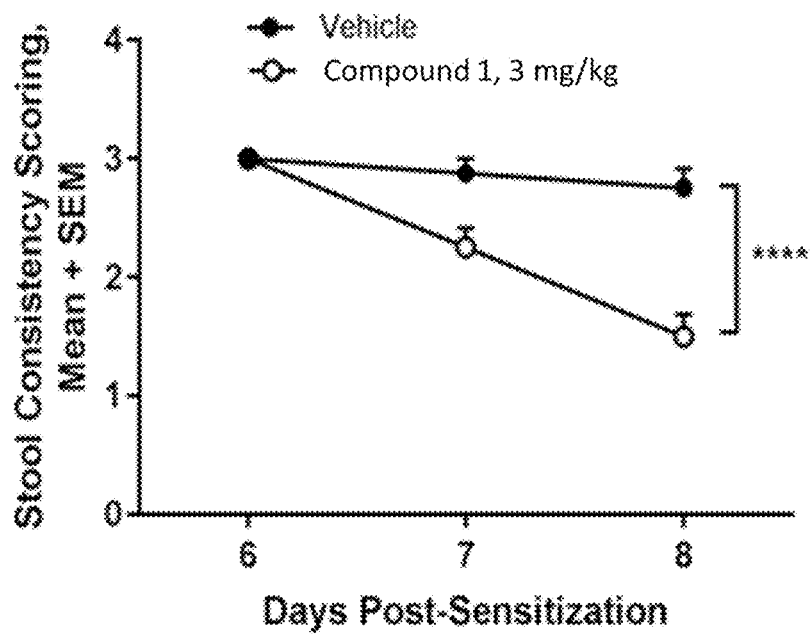
Figure 13C:
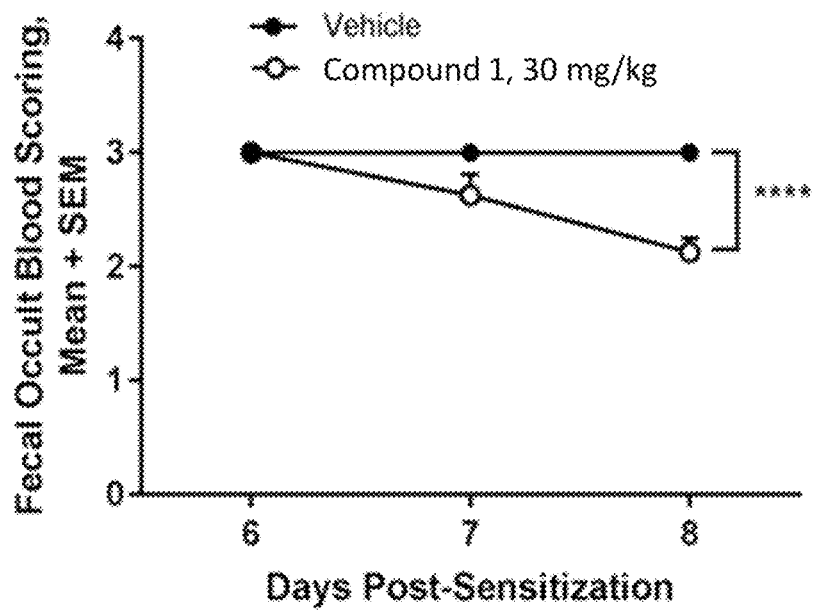
Figure 13D:
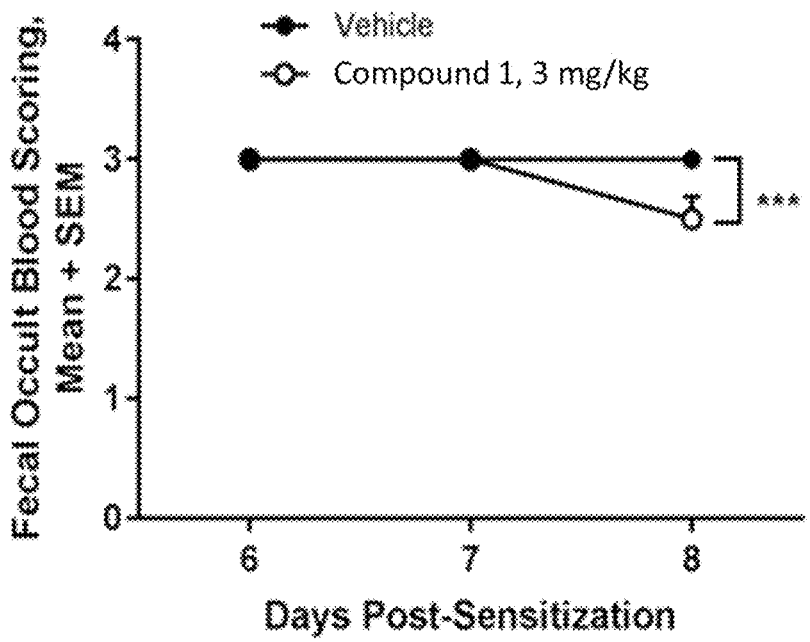
Figure 14A:
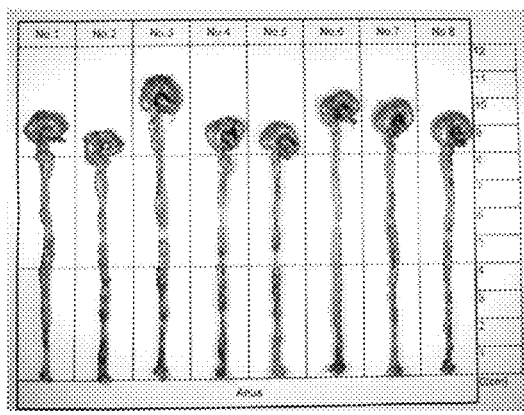
FIGS. 14A-14E show representative images of colon shortening resulting from Compound 1 dosed either orally or directly into the colon compared to vehicle. Oral (FIG. 14B) and intracolonic (FIG. 14D) Compound 1 treatment significantly ameliorated colon shortening as compared to respective vehicle-treated controls (FIGS. 14A, 14C) in oxazolone-induced murine colitis model. Colon length data (FIG. 14E) are graphed as mean+SEM, n=8 per treatment group. SEM: standard error of the mean. ****p<0.0001.
Figure 14B:
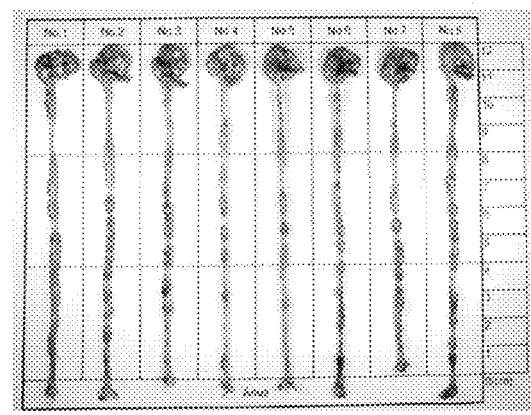
Figure 14C:
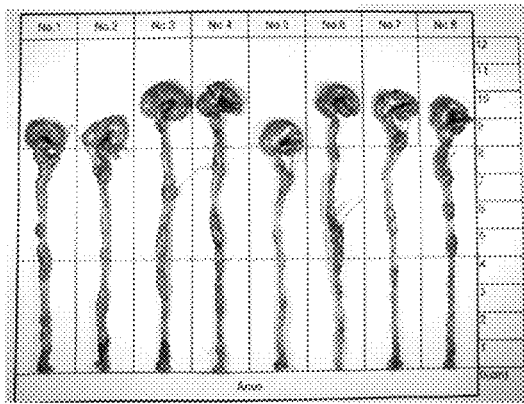
Figure 14D:
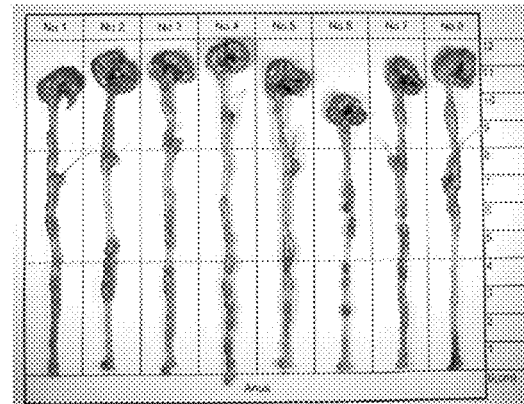
Figure 14E:
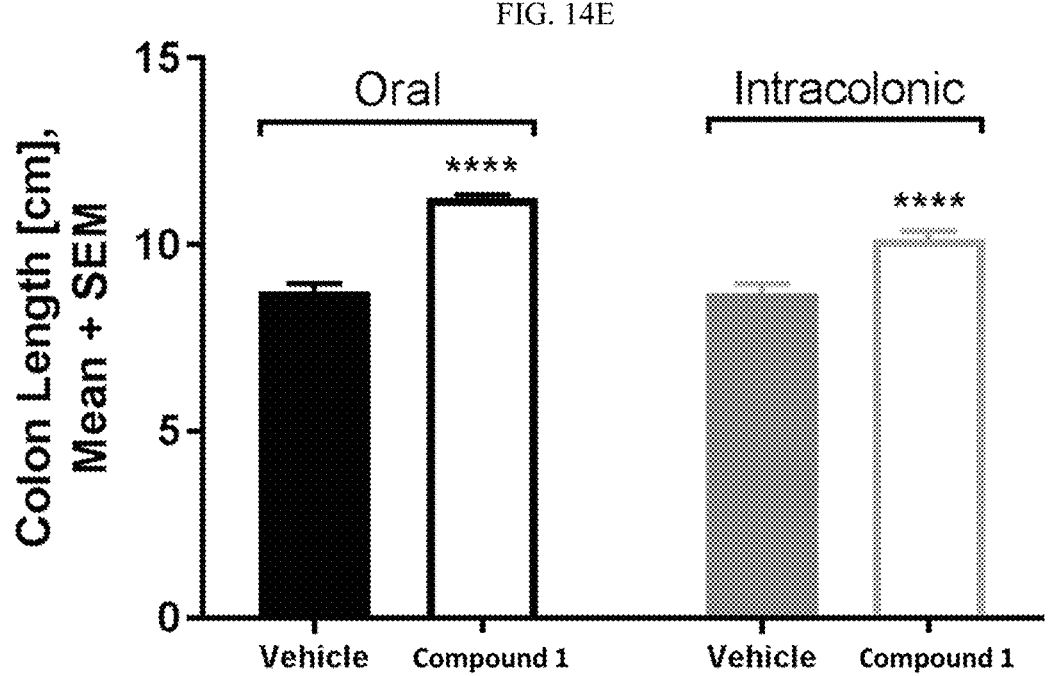

In a further study, quantification of circulating and tissue drug concentrations clearly differentiated the local versus systemic JAK1 target inhibition. Oral dosing resulted in a peak circulating drug level of approximately 11 μM which was similar to the colonic concentration, as shown in FIG. 11C. In contrast, localized Compound 1 delivery was characterized by minimal peak systemic concentrations of approximately 0.04 μM but sustained exposure ≥0.45 μM in the colon tissue, as shown in FIG. 11D. Therefore, strategic targeting or release of JAK1 inhibitors within the inflamed gastrointestinal tissue can potentially achieve improved benefit-risk profiles.

Low dose Compound 1 administered directly to the site of intestinal inflammation was highly efficacious in TNBS-induced colitis, and this treatment response was independent of systemic JAK1 inhibition since Compound 1 plasma concentration was minimal. This data strongly supports the rationale that localized JAK inhibition may be sufficient for achieving treatment response, thereby avoiding the necessity for systemic immune suppression. Without being bound by theory, it is believed these data also suggest that JAK1 is the dominant mechanism driving pathogenesis.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating ulcerative colitis in a subject in need thereof, the method comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof,
wherein the maximum fecal concentration of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile after administering {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or pharmaceutically acceptable salt thereof, is greater than about 25 nM, and
wherein the maximum total plasma concentration of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile after administering {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or pharmaceutically acceptable salt thereof, is less than about 150 nM.

2. A method of treating ulcerative colitis in a subject in need thereof, the method comprising administering to the subject a once-daily dose of about 25 mg to about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein the dose comprises one or more sustained-release dosage forms each comprising the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

3. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

4. The method of claim 2, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

5. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered at a daily dose of from about 50 mg to about 100 mg.

6. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered at a daily dose of from about 25 mg to about 75 mg.

7. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or pharmaceutically acceptable salt thereof, is administered at a daily dose of about 25 mg.

8. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered at a daily dose of about 50 mg.

9. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered at a daily dose of about 100 mg.

10. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered once daily at a dose of about 25 mg.

11. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered twice daily at a dose of about 25 mg for a total daily administration of about 50 mg.

12. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered once daily at a dose of about 50 mg.

13. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered twice daily at a dose of about 50 mg for a total daily administration of about 100 mg.

14. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered once daily at a dose of about 100 mg.

15. The method of claim 1, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is administered as one or more sustained release dosage forms each comprising the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or pharmaceutically acceptable salt thereof.

16. The method of claim 1, wherein the maximum fecal concentration of the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile is greater than about 50 nM after administration of the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

17. The method of claim 1, wherein the maximum total plasma concentration of the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile is less than about 150 nM after administration of the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

18. The method of claim 1, wherein the maximum total plasma concentration of the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile is less than about 141 nM after administration of the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

* * * * *